(12) United States Patent
Matsuba et al.

(10) Patent No.: US 6,861,534 B2
(45) Date of Patent: Mar. 1, 2005

(54) PROCESS FOR PRODUCING 1,3-DIALKYL-2-IMIDAZOLIDINONE COMPOUND

(75) Inventors: Katsuhiko Matsuba, Sodegaura (JP); Takazou Katou, Sodegaura (JP); Satoshi Inoki, Yamaguchi (JP); Hiroyoshi Watanabe, Sodegaura (JP); Takashi Ohkawa, Takaishi (JP); Masato Yamazaki, Takaishi (JP); Michio Iwama, Sodegaura (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 10/203,937

(22) PCT Filed: Dec. 27, 2001

(86) PCT No.: PCT/JP01/11562

§ 371 (c)(1),
(2), (4) Date: Aug. 16, 2002

(87) PCT Pub. No.: WO02/055505

PCT Pub. Date: Jul. 18, 2002

(65) Prior Publication Data

US 2003/0009035 A1 Jan. 9, 2003

(30) Foreign Application Priority Data

| Jan. 4, 2001 | (JP) | 2001-000103 |
| Mar. 30, 2001 | (JP) | 2001-101410 |
| Apr. 2, 2001 | (JP) | 2001-103176 |
| Jul. 6, 2001 | (JP) | 2001-206472 |

(51) Int. Cl.[7] .......................................... C07D 233/06
(52) U.S. Cl. .................................................. 548/316.4
(58) Field of Search ..................................... 548/316.4

(56) References Cited

U.S. PATENT DOCUMENTS

| 4,668,793 A | 5/1987 | Nagata et al. |
| 5,783,706 A | 7/1998 | Henkelmann et al. |

FOREIGN PATENT DOCUMENTS

| JP | 53-073561 A | 6/1978 |
| JP | 60-03299 B2 | 8/1978 |
| JP | 1-15503 B2 | 6/1982 |
| JP | 57-120570 A | 7/1982 |
| JP | 57-175170 A | 10/1982 |
| JP | 57-175170 | 10/1982 |
| JP | 59-155364 A | 9/1984 |
| JP | 60-243071 A | 12/1985 |
| JP | 61-109772 A | 5/1986 |
| JP | 61-172862 A | 8/1986 |
| JP | 07-252230 A | 10/1995 |
| JP | 10-502917 A | 3/1998 |
| JP | 10-330366 A | 12/1998 |
| JP | 10-330366 | 12/1998 |

OTHER PUBLICATIONS

An English translation of JP 10–330366, Dec. 15, 1998.*
Marsella, Ruthenium catalyzed reactions of ethylene glycol with primary amines: steric factors and selectivity control, Journal of Organometallic Chemistry, 1991, pps 97–105, 407, Elsevier Sequoia S.A., Lausanne, Switzerland.
Nomura et al., "Preparation of Cyclic Ureas from Carbon Dioxide and Diamines Catalyzed by Triphenylstibine Oxide," *Ind. Eng. Chem. Res.*, 1987, pp 1056–1059, vol. 26, No. 6, American Chemical Society* XP–002290835.

* cited by examiner

*Primary Examiner*—Laura L. Stockton
(74) *Attorney, Agent, or Firm*—Burns, Doane, Swecker & Mathis, L.L.P.

(57) ABSTRACT

There is provided a process for preparing a 1,3-dialkyl-2-imidazolidinone by using an alkylene oxide as a first component, using at least one of (A) carbon dioxide and a monoalkylamine; (B) a carbon dioxide compound of the monoalkylamine; and (C) an 1,3-dialkylurea, reacting the first and second components by heating at 50° C. or higher to give 1,3-dialkyl-2-imidazolidinone, characterized in that the total molar amount of a molar feed amount of the monoalkylamine included in the component (A), a molar feed amount of the monoalkylamine part of the carbon dioxide compound of monoalkylamine, component (B), and the double of a molar feed amount of the 1,3-dialkylurea, component (C), is at least three folds of a molar feed amount of the alkylene oxide.

The preparation process of this invention uses an industrially readily available alkylene oxide as a starting material and can be suitably conducted with a higher yield in an industrial scale.

16 Claims, 4 Drawing Sheets

PROCESS FOR PRODUCING 1,3-DIALKYL-2-IMIDAZOLIDINONE COMPOUND

TECHNICAL FIELD

This invention relates to a process for preparing 1,3-dialkyl-2-imidazolidinones.

1,3-Dialkyl-2-imidazolidinones have been widely used as an aprotic polar solvent. For example, they are useful as a solvent for a resin such as polyamides, polyesters, polyvinyl chlorides and phenol resins; a solvent for a variety of organic synthetic reactions; or an extraction solvent for extracting an aromatic hydrocarbon from a mixture of hydrocarbons. Among those, 1,3-dimethyl-2-imidazolidinone (hereinafter, sometimes referred to as "DMI") is particularly useful because it exhibits particularly higher resistance to a strong alkali and thus is little decomposed even when heated with an alkali-metal hydroxide solution. It is, therefore, also preferred as a solvent for dehalogenation of an aromatic organohalide.

BACKGROUND ART

Various processes using N,N'-dimethylethylenediamine as a starting material have been proposed for preparing 1,3-dialkyl-2-imidazolidinones; for example, reacting N,N'-dimethylethylenediamine with trichloromethyl chloroformate (JP-A 53-73561); reacting N,N'-dimethylethylenediamine with carbon dioxide (JP-A 57-175170); reacting N,N'-dimethylethylenediamine with phosgene in the presence of water and a dehydrochlorinating agent (JP-A 61-109772 and JP-A 61-172862); and reacting N,N'-dialkylethylenediamine with urea in a polar solvent (JP-A 7-252230). A known process for preparing N,N'-dialkylethylenediamines as a starting material such as N,N'-dimethylethylenediamine described above is based on ethylene dichloride and monomethylamine as described in JP-A 57-120570. The process, however, produces a large amount of salt contaminated with organic compounds as a byproduct, which may cause a difficult issue of disposal. J. Organometallic Chem., 407, 97 (1991) has described a process where ethylene glycol is reacted with monomethylamine in the presence of a homogeneous catalyst comprising ruthenium and triphenylphosphine. Recovery and recycle of a homogeneous noble metal catalyst is, however, industrially difficult. Therefore, a process using N,N'-dialkylethylenediamine as a starting material is not ideal for preparing 1,3-dialkyl-2-imidazolidinone.

In addition, there have been proposed reduction of 2-imidazolidinone and formaldehyde in the presence of a hydrogenation catalyst (JP-A 60-243071) and catalytic reduction of N,N'-hydroxymethylimidazolidinone dialkyl ether (JP-B 60-3299). These processes, however, employ a starting material derived from ethylenediamine. which may also cause the problem described above, and are impractically longer processes.

Alternative processes have been disclosed, including reacting an N-alkylmonoethanolamine and an alkylamine such as monomethylamine with carbon dioxide, an alkylamine alkylcarbamate or 1,3-dialkylurea (JP-A 57-98268); reacting ethylene glycol, carbon dioxide and monomethylamine at an elevated temperature under a higher pressure (JP-A 59-155364); and reacting alkylene carbonate with monoalkylamine (JP-A10-502917). These processes are one-step processes, and an N-alkylmonoethanolamine, ethylene glycol and an alkylene carbonate as starting materials can be readily prepared from an alkylene oxide. These processes are, therefore, noteworthy. These processes have a problem of production of N-alkyldiethanolamines as byproducts during preparing an N-alkylmonoethanolamine from ethylene oxide. JP-A 10-330366 has disclosed a process for preparing DMI by a one-pot reaction from ethylene oxide, which has a problems of a lower yield.

In these processes, a monoalkylamine as a starting material is disproportionated during a reaction to give disproportionation byproducts, i.e., ammonia, a dialkylamine and/or a trialkylamine. JP-B 1-15503 has disclosed a process where ethylene glycol is used as a starting material and unreacted materials containing a monoalkylamine is circulated and recycled in a reactor. In this process, ammonia as a byproduct is also circulated so that repeated circulation may increase ammonia, leading to increase of byproducts such as 1-alkyl-2-imidazolidinones and reduction in an yield of desired 1,3-dialkyl-2-imidazolidinones. Thus, this process has not been industrially available.

DISCLOSURE OF THE INVENTION

An objective of this invention is to provide a process for preparing 1,3-dialkyl-2-imidazolidinones using an industrially readily available alkylene oxide as a starting material with an improved yield which can be suitably practicable in an industrial scale. Another objective of this invention is to provide a process for highly effectively preparing 1,3-dialkyl-2-imidazolidinones by effectively separating or processing byproducts such as N-alkyldiethanolamines, ammonia, dialkylamines, trialkylamines, 1-alkyl-2-imidazolidinones and 1,3-dialkylureas.

The inventors have conducted intense investigation for solving the above problems and have found that these problems can be solved by a process for preparing 1,3-dialkyl-2-imidazolidinones by heating a first component consisting of an alkylene oxide and a second component consisting of at least one of (A) carbon dioxide and a monoalkylamine, (B) a carbon dioxide compound of a monoalkylamine and (C) a 1,3-dialkylurea at 50° C. or higher, wherein the second component is charged such that the total of a molar amount of the charged monoalkylamine in the component (A), a molar amount of the monoalkylamine part in the charged carbon dioxide compound of monoalkylamine, component (B), and the double of a molar amount of the charged 1,3-dialkylurea, component (C), is at least three folds of a molar amount of the charged alkylene oxide, achieving this invention.

This invention provides a process for preparing a 1,3-dialkyl-2-imidazolidinone by using an alkylene oxide represented by formula (1) as a first component:

(1)

wherein in the formula (1), $R^1$ represents hydrogen or alkyl group having 1 to 6 carbon atoms, using at least one selected from the group consisting of the following components (A), (B) and (C) as a second component:

component (A): carbon dioxide and a monoalkylamine represented by formula (2):

$R^2NH_2$  (2)

wherein in the formula (2), $R^2$ represents alkyl group having 1 to 6 carbon atoms;

component (B): a carbon dioxide compound of the monoalkylamine represented by formula (2); and component (C): an 1,3-dialkylurea represented by formula (3):

wherein in the formula (3), $R^2$ is as defined above, and reacting said first component with said second component by heating those components at 50° C. or higher to give 1,3-dialkyl-2-imidazolidinone represented by formula (4):

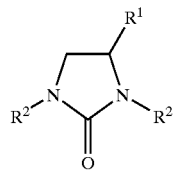

(4)

wherein in the formula (4), $R^1$ and $R^2$ are as defined above, characterized in that the total molar amount of a molar feed amount of the monoalkylamine included in the component (A), a molar feed amount of the monoalkylamine part of the carbon dioxide compound of monoalkylamine, said compound being component (B), and the double of a molar feed amount of the 1,3-dialkylurea, said 1,3-dialkylurea being component (C), is at least three folds of a molar feed amount of said alkylene oxide.

The reaction is preferably conducted under a pressure of 4 MPa or higher.

It is also preferable that the total molar amount of a molar feed amount of the carbon dioxide included in the component (A), a molar feed amount of the carbon dioxide part of the carbon dioxide compound of monoalkylamine, said compound being the component (B) and a molar feed amount of the 1,3-dialkylurea, said 1,3-dialkylurea being the component (C), is at least one and half folds of a molar feed amount of said alkylene oxide.

It is also preferable that $R^1$ is hydrogen atom; $R^2$ represents methyl; and the 1,3-dialkyl-2-imidazolidinone prepared is 1,3-dimethyl-2-imidazolidinone.

In this process, it is also preferable that ethylene oxide is used as said first component and at least one selected from the group consisting of the following components (D), (E) and (F) is used as said second component:

component (D): carbon dioxide and monomethylamine;

component (E): a carbon dioxide compound of monomethylamine; and component (F): 1,3-dimethylurea, the process comprises:

(1) a 1,3-dimethyl-2-imidazolidinone preparation step of preparing 1,3-dimethyl-2-imidazolidinone by heating said first component and said second component at 50° C. or higher, and the process further comprises:

(2) a first separation step of separating the reaction mixture obtained in the 1,3-dimethyl-2-imidazolidinone preparation step into a first fraction containing monomethylamine, carbon dioxide and a carbon dioxide compound of monomethylamine as main components, and also containing water; and a second fraction containing 1,3-dimethyl-2-imidazolidinone and high-boiling compounds with a higher boiling point than that of 1,3-dimethyl-2-imidazolidinone as main components, and also containing water;

(3) a second separation step of separating at least part of the second fraction in the first separation step into a first fraction containing water and low-boiling amines with a boiling point higher than that of water and lower than that of 1,3-dimethyl-2-imidazolidinone as main components; and a second fraction containing 1,3-dimethyl-2-imidazolidinone and said high-boiling compounds as main components;

(4) a third separation step of separating the second fraction in the second separation step into a first fraction containing 1,3-dimethyl-2-imidazolidinone as a main component; and a second fraction containing said high-boiling compounds as main components; and (5) a fourth separation step of separating the first fraction in the first separation step into a first fraction containing ammonia, dimethylamine, trimethylamine, a carbon dioxide compound of ammonia, a carbon dioxide compound of dimethylamine and a carbon dioxide compound of trimethylamine as main components, and also containing water; and a second fraction containing monomethylamine and a carbon dioxide compound of monomethylamine as main components, and also containing water, where at least part of the second fraction in the fourth separation step is supplied in the 1,3-dimethyl-2-imidazolidinone preparation step.

Furthermore, the above 1,3-dimethyl-2-imidazolidinone preparation step may be carried out by:

(6) a first reaction step of heating ethylene oxide and at least one selected from the group consisting of the components (D), (E) and (F) at 50° C. or higher to prepare N-methyldiethanolamine and 2-(methylamino) ethanol; and (7) a second reaction step of heating N-methyldiethanolamine and 2-(methylamino)ethanol prepared in the first reaction step with at least one selected from the group consisting of the components (D), (E) and (F) at 100° C. or higher to prepare 1,3-dimethyl-2-imidazolidinone, and the second fraction in the fourth separation step may be supplied in said first reaction step and/or said second reaction step.

In the fourth separation step, at least part of the first fraction in the first separation step may be contacted with carbon dioxide, heated at 50° C. or higher, and separated by vapor-liquid separation to remove the first fraction in the fourth separation step into the gaseous phase and obtain the second fraction in the fourth separation step from the liquid phase.

Figure 1:
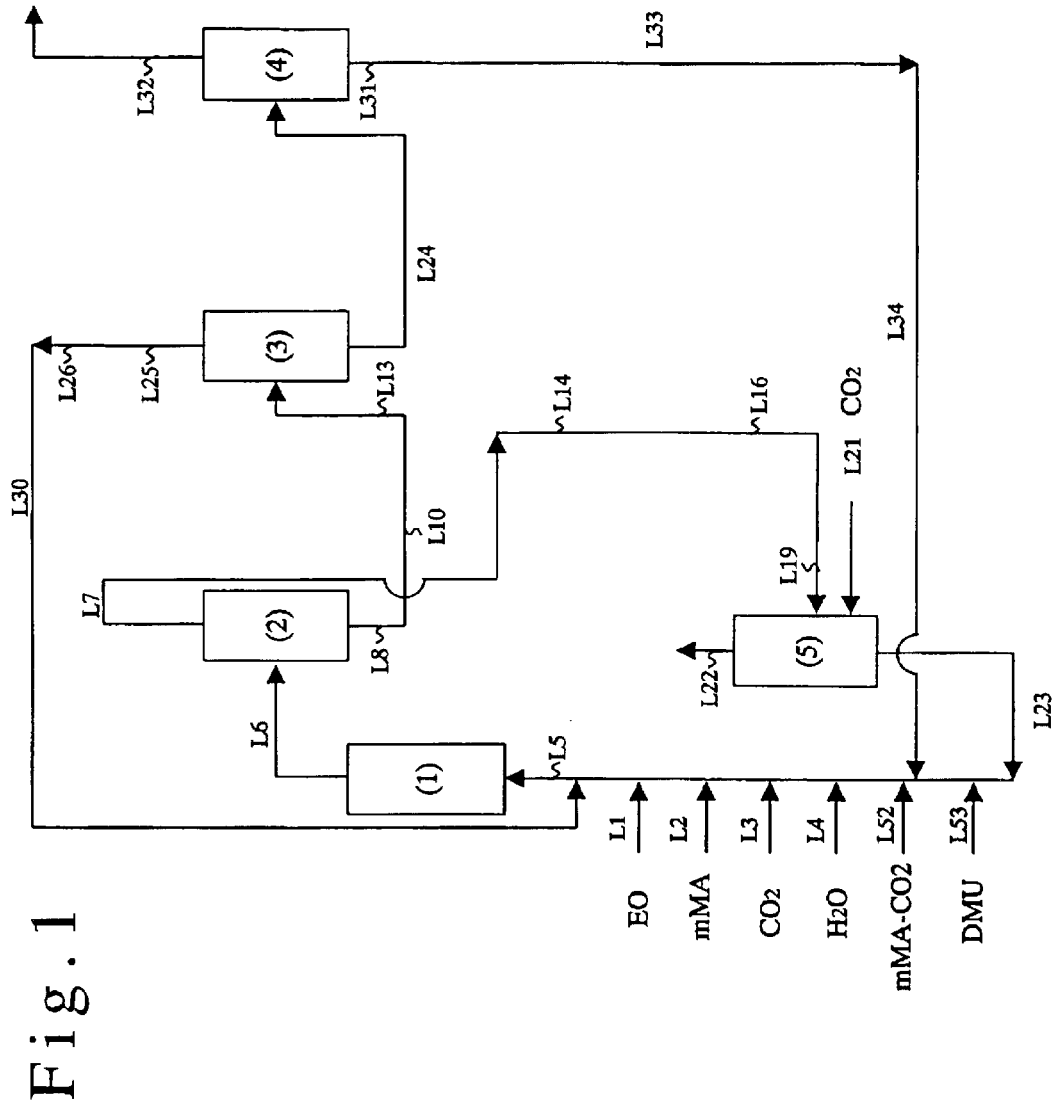
FIG. 1 is a block diagram showing an embodiment of a preparation process according to this invention.

In these drawings, symbols represent the followings: 1: the 1,3-dimethyl-2-imidazolidinone preparation step; 2: the first separation step; 3: the second separation step; 4: the third separation step; 5: the fourth separation step; 6: the first reaction step; 7: the second reaction step; 8: a seventh separation step; 9: a hydrolysis step; 10: an absorption step; 11: a fifth separation step; 12: a rectification step; 13: a sixth separation step.

BEST MODE FOR CARRYING OUT THE INVENTION

Hereinafter, this invention will be described in detail.

This invention provides a process for preparing a 1,3-dialkyl-2-imidazolidinone.

According to the process of this invention, the 1,3-dialkyl-2-imidazolidinone is prepared by reacting the first component consisting of an alkylene oxide represented by the formula (1); and the second component consisting of at least one selected from the group consisting of:

component (A): carbon dioxide and a monoalkylamine represented by the formula (2);

component (B): a carbon dioxide compound of the monoalkylamine represented by the formula (2);

component (C): a 1,3-dialkylurea represented by the formula (3), by heating those components at 50° C. or higher.

An alkylene oxide used as a starting material in the process of this invention is an alkylene oxide in which a straight or circular alkyl group represented by $R^1$ has 1 to 6 carbon atoms, including, for example, ethylene oxide, propylene oxide, ethyloxirane, propyloxirane, (1-methylethyl) oxirane, cyclopropyloxirane, (1,1-dimethylethyl)oxirane, n-butyloxirane, (2-methylpropyl)oxirane, (1-methylpropyl) oxirane, (1-methylcyclopropyl)oxirane, (1,2-dimethylpropyl)oxirane, n-pentyloxirane, (2-methylbutyl) oxirane, (1-ethylpropyl)oxirane, (3-methylbutyl)oxirane, (1-methylbutyl)oxirane, (2,2-dimethylpropyl)oxirane, cyclopentyloxirane, (3,3-dimethylbutyl)oxirane, (1,1-dimethylbutyl)oxirane, (1-methylpentyl)oxirane, n-hexyloxirane, cyclopentylmethyloxirane and cyclohexyloxirane. Among these, ethylene oxide or propylene oxide is preferable and ethylene oxide is more preferable because a 1,3-dialkyl-2-imidazolidinone or 1,3-dialkylpropyleneurea as a product has a variety of applications.

A monoalkylamine represented by the formula(2) which is one of the second component in this invention, is a monoalkylamine in which a straight or circular alkyl group represented by $R^2$ has 1 to 6 carbon atoms, including, for example, monomethylamine, monoethylamine, mono(n-propyl)amine, mono (iso-propyl) amine, mono (n-butyl) amine, mono (sec-butyl) amine, mono(iso-butyl) amine, mono (tert-butyl) amine, mono (n-amyl) amine, mono(1-methylbutyl)amine, mono(2-methylbutyl)amine, mono (iso-amyl) amine, mono (tert-amyl) amine, mono(neo-pentyl) amine, mono (1,2-dimethylpropyl) amine, mono(1-ethylpropyl)amine, mono (n-hexyl) amine and monocyclohexylamine. Among these, monomethylamine or monoethylamine is preferable and monomethylamine is more preferable because 1,3-dimethyl-2-imidazolidinones or 1,3-diethyl-2-imidazolidinones have a variety of applications.

A carbon dioxide compound of monoalkylamine, which is one of the second component in the process of this invention, includes, for example, carbonates, hydrogencarbonates and alkyl carbamates of monoalkylamine.

The carbon dioxide compound of monoalkylamine may be used as a solid or a solution such as an aqueous solution. Alternatively, components which generate the carbon dioxide compound in the reaction system can be used in combination.

1,3-Dialkylurea represented by the formula (3) which is one of the second component in the process of this invention, is 1,3-dialkylurea in which an alkyl group represented by $R^2$ has 1 to 6 carbon atoms, including, for example, 1,3-dimethylurea, 1,3-diethylurea, 1,3-di(n-propyl)urea, 1,3-di(iso-propyl)urea, 1,3-di(n-butyl)urea, 1,3-di(sec-butyl)urea, 1,3-di(iso-butyl)urea, 1,3-di(tert-butyl)urea, 1,3-di(n-amyl)urea, 1,3-di(1-methylbutyl)urea, 1,3-di(2-methylbutyl)urea, 1,3-di(iso-amyl)urea, 1,3-di(tert-amyl)urea, 1,3-di(neo-pentyl)urea, 1,3-di(1,2-dimethylpropyl)urea, 1,3-di(1-ethylpropyl)urea, 1,3-di(n-hexyl)urea and 1,3-dicyclohexylurea. Among these, 1,3-dimethylurea or 1,3-diethylurea is preferable and 1,3-dimethylurea is more preferable because a 1,3-dialkyl-2-imidazolidinone or 1,3-dialkylpropyleneurea as a product has a variety of applications.

The 1,3-dialkylurea may be used as is commercially available or as a solution such as an aqueous solution. Alternatively, components which generate the 1,3-dialkylurea in the reaction system may be used in combination.

The amount of the second component supplied for the reaction in the process of this invention is determined such that the total molar amount of the following i) to iii) included in the second component recovered and recycled and in the second component newly supplied to a reactor is preferably at least three folds, more preferably 3 to 40 folds both inclusive of the molar amount of the alkylene oxide:

i) the molar amount of the monoalkylamine;

ii) the molar amount of the monoalkylamine part in the carbon dioxide compound of the monoalkylamine; and iii) the double of the molar amount of 1,3-dialkylurea.

The reaction can be conducted under the conditions departing from the above range, but the total molar amount of less than three folds may lead to reduction in an yield of the 1,3-dialkyl-2-imidazolidinone. The total molar amount of more than 40 folds may be disadvantageous because of reduction in a volumetric efficiency of a reactor, and increase in a cost for recovery of the unreacted monoalkylamine, carbon dioxide compound of the monoalkylamine and 1,3-dialkylurea. Without recovering and recycling, it is sufficient to consider only the second component newly supplied into the reactor.

Since DMI as a product has a variety of applications as a solvent, it is most preferable to use ethylene oxide as an alkylene oxide, monomethylamine as a monoalkylamine, a carbon dioxide compound of monomethylamine as a carbon dioxide compound of monoalkylamine, and 1,3-dimethylurea as a 1,3-dialkylurea.

In a reaction in the process of this invention, a reaction system can be replaced or pressurized with a gas.

In terms of a pressure, a pressure at a reaction temperature is preferably 4 MPa or higher. Although the reaction may be conducted at a pressure of less than 4 MPa, it may be disadvantageous because of tendency to reduction in a production efficiency of a 1,3-dialkyl-2-imidazolidinone.

As a gas for replacement or pressurization as described above, carbon dioxide is preferable because it can be also used as the second component, but another gas including an inert gas such as nitrogen and argon can be appropriately used. Using carbon dioxide results in improvement in an yield of a 1,3-dialkyl-2-imidazolidinone. Carbon dioxide may be used as gaseous, liquid, solid or supercritical carbon dioxide. The amount of carbon dioxide supplied in this reaction is determined such that the total molar amount of carbon dioxide used for displacement or pressurization and the following iv) to vi) included in the second component recovered and recycled and in the second component newly supplied is preferably at least one and half folds, more preferably 4 to 100 folds both inclusive of the molar amount of the alkylene oxide supplied:

iv) the molar amount of carbon dioxide;
v) the molar amount of carbon dioxide part in the carbon dioxide compound of alkylamine; and
vi) the molar amount of 1,3-dialkylurea.

The total molar amount of less than one and half folds is disadvantageous because of tendency to reduction in a production efficiency for the 1,3-dialkyl-2-imidazolidinone, while the total molar amount of more than 100 folds may be disadvantageous because of tendency to reduction in a volumetric efficiency of the reactor.

A reaction in the process of this invention is conducted at 50° C. or higher, preferably 50 to 300° C. both inclusive. A temperature of lower than 50° C. may be disadvantageous because of tendency to reduction in a production efficiency for the 1,3-dialkyl-2-imidazolidinone, while a temperature of higher than 300° C. may be disadvantageous because of tendency to increase in byproducts.

A reaction time depends on factors such as the amounts of starting materials and a reaction temperature; preferably 200 hours or less, more preferably 0.01 to 100 hours both inclusive, further preferably 0.1 to 50 hours both inclusive. A time of less than 0.01 hours may be disadvantageous because of tendency to reduction in an yield of a 1,3-dialkyl-2-imidazolidinone, while a time of more than 200 hours may be disadvantageous because of tendency to reduction in a volumetric reaction efficiency.

A reaction in the process of this invention may be conducted neat or sometimes using a solvent. Any solvent which is inert to reaction substrates under the reaction condition may be used; preferably, water, hydrocarbons, ethers, amides, circular ureas and supercritical carbon dioxide. Among these, water or a 1,3-dialkyl-2-imidazolidinone which is identical to the product is more preferable because it can eliminate an additional step of recovering a solvent because it is a reaction product.

These solvents may be used alone or in combination of two or more. Depending on a solvent used, the reaction may be conducted in a multiphase system of two or more phases.

The solvent may be suitably used in an amount sufficient to dissolve a part of at least one of the starting materials used. The amount is preferably 100 parts by weight or less, more preferably 50 parts by weight or less to one part by weight of an alkylene oxide as a starting material. An amount of more than 100 parts by weight is disadvantageous because of tendency to reduction in a volumetric efficiency.

In the process of this invention, a catalyst or additive may be used for further improving an yield or reaction rate.

A reactor used for a reaction in the process of this invention may be made of an appropriate known material, and a reactor whose inner wall is at least partly made of the following material (I) is preferable because it may provide a 1,3-dialkyl-2-imidazolidinone with a higher yield:

(I) a metal and/or its oxide containing at least one selected from the group consisting of titanium and zirconium.

Examples of such a reactor include those totally made of a metal containing titanium or zirconium; those whose inner wall is at least partly coated with a metal or its oxide containing titanium or zirconium. Examples of a metal containing titanium or zirconium include industrial pure titanium in JIS Groups 1 to 4; anticorrosion titanium alloys such as Ti-0.15Pd, Ti-5Ta and Ti-0.3Mo-0.8Ni; α-type titanium alloys such as Ti-2.5Sn, Ti-5Al-2.5Sn, Ti-5Al-2.5Sn (ELI), Ti-2.5Cu, Ti-2O-1N-5Fe, Ti-5Ni-0.5Ru, Ti-0.5Pd-3Co and Ti-5.5Al-3.5Sn-3Zr-1Nb-0.3Mo-0.3Si; near α-type titanium alloys such as Ti-8Al-1Mo-1V, Ti-2.25Al-11Sn-5Zr-1Mo-0.2Si, Ti-6Al-2Sn-4Zr-2Mo, Ti-5Al-5Sn-2Zr-2Mo-0.25Sn, Ti-6Al-2Nb-1Ta-0.8Mo, Ti-6Al-5Zr-0.5Mo-0.2Si and Ti-4.5Al-3V-2Fe-2Mo; α+β-type titanium alloys such as Ti-5Al-2Cr-1Fe, Ti-5Al-5Sn-5Zr-2Cr-1Fe, Ti-4Al-4Mn, Ti-3Al-2.5V, Ti-6Al-4V, Ti-6Al-4V(ELI), Ti-6Al-6V-2Sn, Ti-6Al-2Sn-4Zr-6Mo, Ti-7Al-4Mo, Ti-5Al-2Zr-4Mo-4Cr, Ti-6Al-1.7Fe-0.1Si, Ti-6.4Al-1.2Fe, Ti-15Zr-4Nb-2Ta-2Pd, Ti-6Al-7Nb and Ti-8Mn; β-type titanium alloys such as Ti-13V-11Cr-3Al, Ti-15Mo-5Zr, Ti-15Mo-0.2Pd, Ti-15V-3Cr-3Sn-3Al, Ti-20V-4Al-1Sn, Ti-22V-4Al and Ti-16V-4Sn-3Al-3Nb; near β-type titanium alloys such as Ti-10V-2Fe-3Al and Ti-9.5V-2.5Mo-3Al; zirconium alloys such as zircaloy-2, zircaloy-4, Zr-2.5Nb and ozenite. Among these metals, titanium-containing metals are preferable and industrial pure titanium or an anticorrosion titanium alloy is more preferable.

In the process of this invention, an alkylene oxide and a monoalkylamine are reacted to give a 1,3-dialkyl-2-imidazolidinone via corresponding N-alkylmonoethanolamine and N-alkyldiethanolamine as intermediates. According to the process of this invention, a 1,3-dialkyl-2-imidazolidinone can be, therefore, prepared by forming an N-alkylmonoethanolamine and N-alkyldiethanolamine at 50° C. or higher and then reacting these products at a further higher temperature. In such a case, the 1,3-dialkyl-2-imidazolidinone may be formed not only from the N-alkylmonoethanolamine but also from the N-alkyldiethanolamine. Thus, it is not necessary to separate these.

Any style of the process of this invention may be employed as long as starting materials used can be effectively mixed and contacted with other material. Any of batch, semi-batch and continuous flow systems may be employed; for example, charging all materials together in a reactor, continuous or intermittent feeding of at least one material into the other materials, or continuously or intermittently feeding all materials. Alternatively, after mixing the first component and a part of the second component, then the mixture may be fed into a reactor. In such a case, a reaction may proceed in a feed line, and an N-alkylmonoethanolamine and/or an N-alkyldiethanolamine may be formed in the line.

In the process of this invention, a product solution may be, if necessary, treated as usual, for example, by distillation or crystallization to provide a desired 1,3-dialkyl-2-imidazolidinone.

Figure 2:
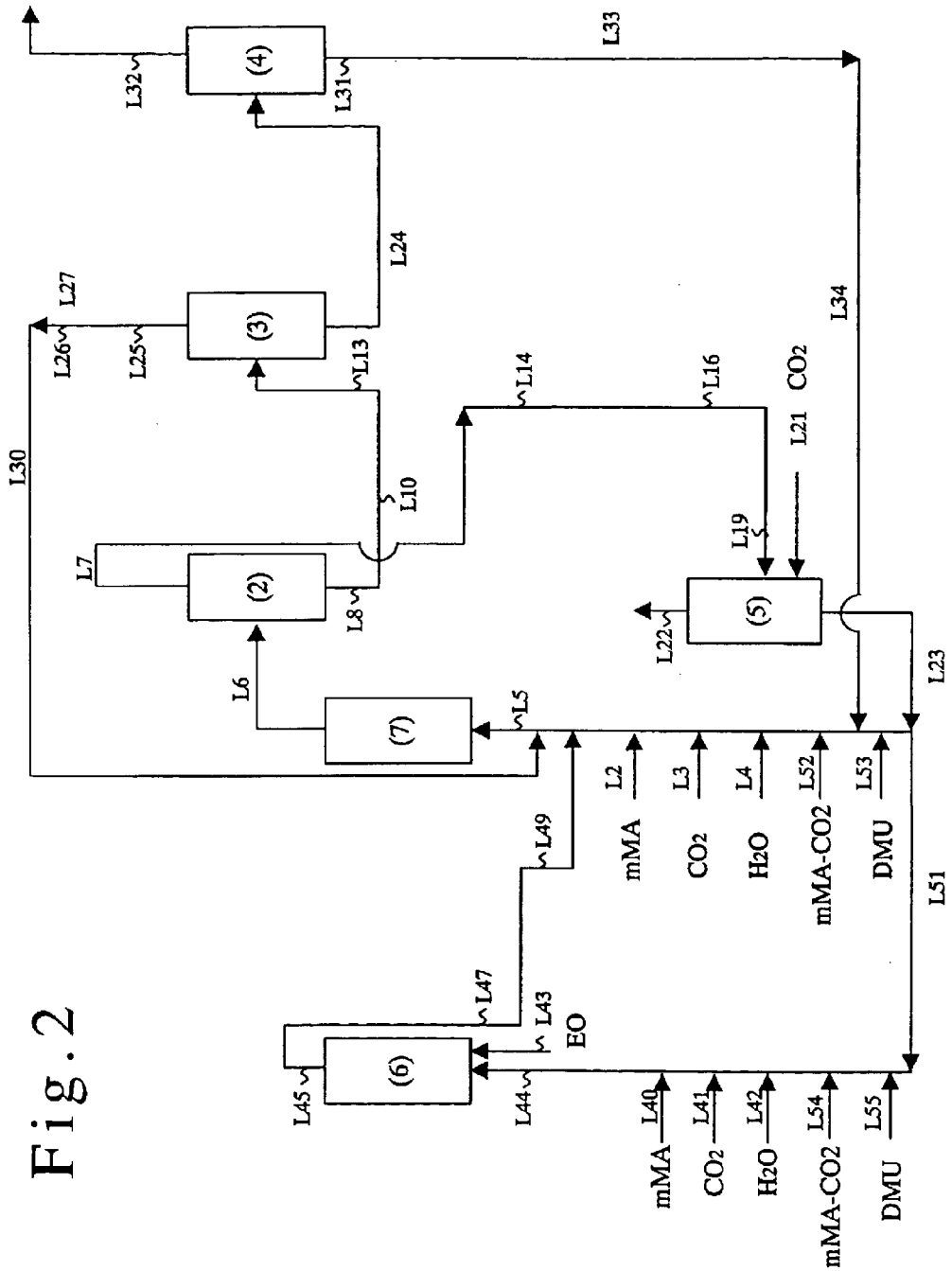
FIG. 2 is a block diagram showing another embodiment of a preparation process according to this invention.
Figure 3:
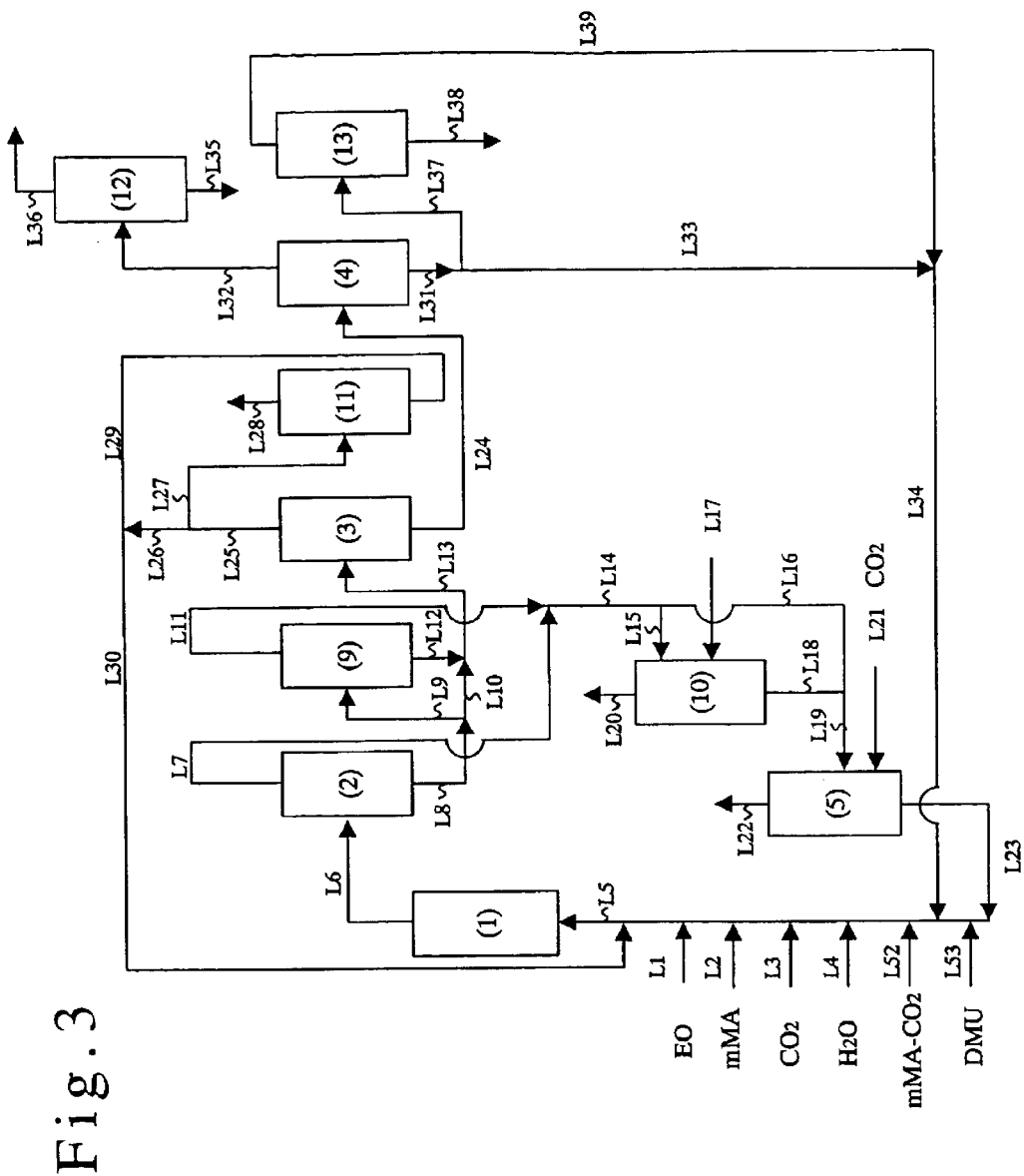
FIG. 3 is a block diagram showing another embodiment of a preparation process according to this invention.
Figure 4:
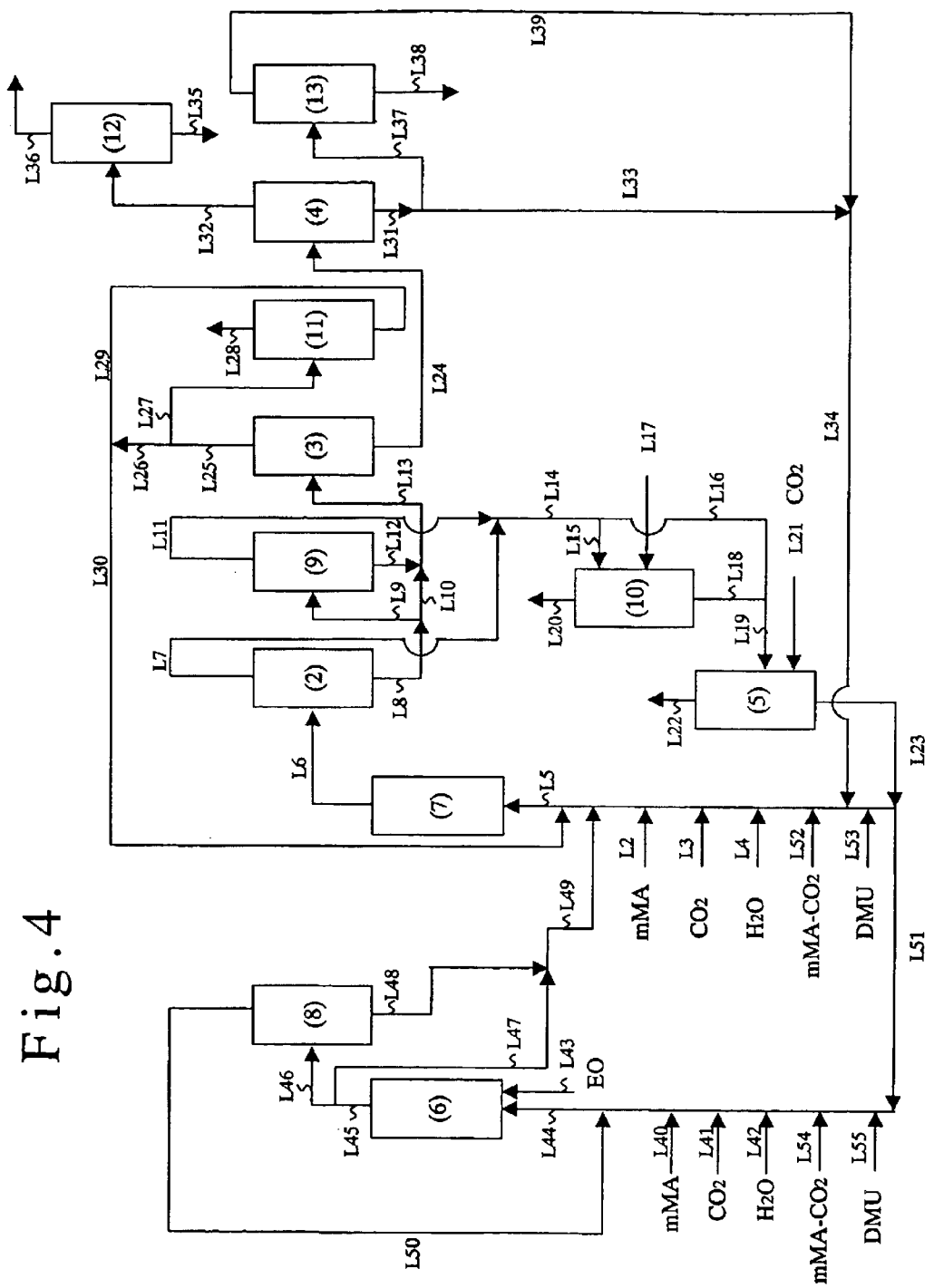
FIG. 4 is a block diagram showing another embodiment of a preparation process according to this invention.

When a 1,3-dialkyl-2-imidazolidinone prepared by the process of this invention is DMI, it is preferably prepared according to a process flow shown in FIG. 1 or 2. FIGS. 3 and 4 show the embodiments in FIGS. 1 and 2 with additional steps for further improving a production efficiency or purity for DMI.

This invention will be described with reference to FIGS. 3 and 4.

As shown in FIG. 3, in 1,3-dimethyl-2-imidazolidinone preparation step (1), ethylene oxide, monomethylamine as one compound of the component (D) and carbon dioxide as another compound of the component (D) are fed to the 1,3-dimethyl-2-imidazolidinone preparation step via lines L1, L2 and L3, respectively. The components (E) and/or (F)

may be used in place of or in addition to the component (D). In such a case, a carbon dioxide compound of monomethylamine as the component (E) is fed to the 1,3-dimethyl-2-imidazolidinone preparation step via line 52, while 1,3-dimethylurea as the component (F) is fed via line 53. Ethylene oxide, monomethylamine, carbon dioxide, the carbon dioxide compounds of monomethylamine and 1,3-dimethylurea may be fed by mixing at least two of these in line L5 before introducing to the preparation step (1) or by directly introducing into a reactor without line L5. When employing mixing in line L5, line L5 may be heated for promoting a reaction in the line.

In these figures, EO represents ethylene oxide; mMA represents monomethylamine; mMA-CO2 represents a carbon dioxide compound of monomethylamine; and DMU represents 1,3-dimethylurea.

In the 1,3-dimethyl-2-imidazolidinone preparation step, the amount of the second component supplied to the reaction is determined such that the total of the following i') to iii') is preferably at least three folds, more preferably 3 to 40 folds both inclusive of the molar amount of ethylene oxide supplied. This molar ratio of less than 3 folds may be disadvantageous because of tendency to reduction in an yield of 1,3-dimethyl-2-imidazolidinone, while that of more than 40 folds may be disadvantageous because of increase in a cost for recovering unreacted monomethylamine, the carbon dioxide compound of monomethylamine and 1,3-dimethylurea:

i') the total of the molar amount of monomethylamine recovered and recycled and the molar amount of monomethylamine newly supplied;

ii') the total of the molar amount of monomethylamine part in the carbon dioxide compound of monomethylamine recovered and recycled and the molar amount of monomethylamine part in the carbon dioxide compound of monomethylamine newly supplied; and iii') the total of the double of the molar amount of 1,3-dimethylurea recovered and recycled and the double of the molar amount of 1,3-dimethylurea newly supplied.

Carbon dioxide used in the 1,3-dimethyl-2-imidazolidinone preparation step may be used as gaseous, liquid, solid or supercritical carbon dioxide. Carbon dioxide discharged from lines L20 and L22 may be recovered for recycling.

The amount of the second component supplied for this reaction is determined such that the total of the following iv') to vi') is preferably at least one and half folds, more preferably 4 to 100 folds both inclusive of the molar amount of ethylene oxide supplied. This molar ratio of less than one and half folds is disadvantageous because of tendency to reduction in a production efficiency for the 1,3-dialkyl-2-imidazolidinone, while the molar ratio of more than 100 folds may be disadvantageous because of tendency to reduction in a volumetric efficiency of the reactor:

iv') the total of the molar amount of carbon dioxide part in the carbon dioxide compound of monomethylamine recovered and recycled and the molar amount of carbon dioxide part in the carbon dioxide compound of monomethylamine newly supplied;

v') the total of the molar amount of 1,3-dimethylurea recovered and recycled and the molar amount of 1,3-dimethylurea newly supplied; and vi') the total of the molar amount of carbon dioxide recovered and recycled and the molar amount of carbon dioxide newly supplied.

The reaction in the 1,3-dimethyl-2-imidazolidinone preparation step is conducted at 50° C. or higher, preferably 50 to 300° C. both inclusive. A temperature of lower than 50° C. leads to reduction in a production efficiency for DMI. A temperature of higher than 300° C. may be disadvantageous because of tendency to increase in byproducts.

A pressure depends on factors such as a temperature and starting materials; preferably 4 MPa to 30 MPa both inclusive. A pressure of less than 4 MPa may be disadvantageous because of tendency to reduction in a production efficiency for 1,3-dimethyl-2-imidazolidinone, while a pressure of more than 30 MPa may be disadvantageous because of increase in a production cost of a reactor.

A reaction time depends on factors such as the amounts of starting materials and a reaction temperature; preferably 200 hours or less, more preferably 0.01 to 100 hours both inclusive, more preferably 0.1 to 50 hours both inclusive. A time of less than 0.01 hours may be disadvantageous because of tendency to reduction in an yield of 1,3-dimethyl-2-imidazolidinone, while a time of more than 200 hours may be disadvantageous because of tendency to reduction in a volumetric reaction efficiency.

In the 1,3-dimethyl-2-imidazolidinone preparation step, the reaction may be conducted in the presence of water, which is introduced via lines L4 and L5. The amount of water supplied to the reaction is determined such that the amount of water recovered and recycled and water newly supplied is preferably 100 parts by weight or less, more preferably 50 parts by weight or less to one part by weight of ethylene oxide supplied. The amount of more than 100 parts by weight is disadvantageous because of reduction in a volumetric efficiency of the reactor.

The 1,3-dimethyl-2-imidazolidinone preparation step may be carried out by two steps, as shown in FIG. 4, i.e., a first reaction step (6) for preparing 2-(methylamino)ethanol and N-methyldiethanolamine; and a second reaction step (7) for preparing DMI from 2-(methylamino)ethanol and N-methyldiethanolamine prepared in the first reaction step (6).

In this case, to the first reaction step are fed ethylene oxide via lines L43, monomethylamine as one compound in the component (D) via line L40 and carbon dioxide as another compound in the component (D) via line L41. Alternatively, the component (E) and/or (F) may be used in place of or in addition to the component (D). In such a case, the carbon dioxide compound of monomethylamine as the component (E) is fed via line L54 to the first reaction step while 1,3-dimethylurea as the component (F) is fed via line L55. Ethylene oxide, monomethylamine, carbon dioxide, the carbon dioxide compound of monomethylamine and 1,3-dimethylurea may be fed by mixing at least two of these in line L44 before introducing to the first reaction step or by directly introducing into a reactor without line L44. When employing mixing in line L44, line L44 may be heated for promoting a reaction in the line.

In the first reaction step, 2-(methylamino) ethanol and N-methyldiethanolamine are prepared by conducting the reaction at 50° C. or higher. A temperature of lower than 50° C. is disadvantageous because of tendency to reduction in a production efficiency for 2-(methylamino)ethanol.

A pressure in the first reaction step depends on factors such as a temperature and starting materials; preferably 0.4 MPa or more. A pressure of less than 0.4 MPa may be disadvantageous because of tendency to reduction in a consumption rate for ethylene oxide.

A reaction mixture containing 2-(methylamino)ethanol and N-methyldiethanolamine prepared in the first reaction step and unreacted monomethylamine can be directly fed via lines L45, L47 and L49 to the second reaction step. The reaction mixture can be fed to the second reaction step after being fed to line L5 and being premixed with other materials such as monomethylamine, carbon dioxide, the carbon dioxide compound of monomethylamine, 1,3-dimethylurea and/or water supplied via L2, and so on.

In the process of this invention, the amount of the second component supplied to the first reaction step is determined such that the total molar amount of the following i") to iii") is preferably at least three folds, more preferably 3 to 40 folds both inclusive of the molar amount of ethylene oxide supplied. This molar ratio of less than 3 folds may be disadvantageous because of tendency to reduction in an yield of 1,3-dimethyl-2-imidazolidinone, while that of more than 40 folds may be disadvantageous because of reduction in a volumetric efficiency of a reactor, and increase in a cost for recovery of the unreacted monomethylamine and the carbon dioxide compound of monomethylamine:

i") the total of the molar amount of monomethylamine recovered and recycled and the molar amount of monomethylamine newly supplied;

ii") the total of the molar amount of monomethylamine part in the carbon dioxide compound of monomethylamine recovered and recycled and the molar amount of monomethylamine newly supplied in the carbon dioxide compound of monomethylamine; and iii") the total of the double of the molar amount of 1,3-dimethylurea recovered and recycled and the double of the molar amount of 1,3-dimethylurea newly supplied.

Carbon dioxide used in the first reaction step may be used as gaseous, liquid, solid or supercritical carbon dioxide. The amount of the second component supplied to the first reaction step is determined such that the total molar amount of the following iv") to vi") is preferably 100 folds or less of the molar amount of ethylene oxide supplied. This molar ratio of more than 100 folds may be disadvantageous because of tendency to reduction in a volumetric efficiency of the reactor:

iv") the total of the molar amount of carbon dioxide part in the carbon dioxide-compound of monomethylamine recovered and recycled and the molar amount of carbon dioxide part in the carbon dioxide compound of monomethylamine newly supplied;

v") the total of the molar amount of carbon dioxide recovered and recycled and the molar amount of carbon dioxide newly supplied; and vi") the total of the molar amount of 1,3-dimethylurea recovered and recycled and the molar amount of 1,3-dimethylurea newly supplied.

In the first reaction step, the reaction may be conducted in the presence of water, which is introduced via line L42. The amount of water supplied is preferably 100 parts by weight or less, more preferably 50 parts by weight or less to one part by weight of ethylene oxide supplied. The amount of more than 100 parts by weight is disadvantageous because of reduction in a volumetric efficiency.

The process of this invention may comprise a seventh separation step (8). In such a case, a part or all of the reaction mixture prepared in the first reaction step may be fed to the seventh separation step via lines L45 and L46. In the seventh separation step, a first fraction containing unreacted monomethylamine as a main component and a second fraction containing 2-(methylamino)ethanol and N-methyldiethanolamine as main components are separated from the reaction mixture. The first fraction may be circulated to the first reaction step via line L50. The second fraction is fed to the second reaction step via lines L48 and L49. The second fraction may be fed to the second reaction step after feeding the fraction to line L5 and premixing it with other materials such as monomethylamine, carbon dioxide and/or water from, for example, line L2.

To the second reaction step can be fed the reaction mixture obtained in the first reaction step via lines L47 and L49 and/or the second fraction in the seventh separation step via lines L48 and L49, to feed 2-(methylamino)ethanol and N-methyldiethanolamine produced in the first reaction step to the second reaction step. When feeding at least one of unreacted components (D), (E) and (F) to the second reaction step, the second reaction step may be conducted as such. Further, to the second reaction step may be supplied monomethylamine via line L2, carbon dioxide via line L3, the carbon dioxide compound of monomethylamine via line L52 and/or 1,3-dimethylurea via line L53. To the second reaction step may be supplied the reaction mixture in the first reaction step, the second fraction in the seventh separation step, monomethylamine, carbon dioxide, the carbon dioxide compound of monomethylamine, 1,3-dimethylurea and/or water after mixing at least two of them.

In the second reaction step, the reaction is conducted at 100° C. or higher, preferably 100° C. to 300° C. both inclusive, preferably with a residence time of 1 to 24 hours both inclusive. A reaction temperature of less than 100° C. is disadvantageous because of tendency to reduction in a production efficiency for 1,3-dimethyl-2-imidazolidinone while a temperature of more than 300° C. is disadvantageous because of tendency to reduction in an yield of 1,3-dimethyl-2-imidazolidinone. A residence time of less than 1 hour is disadvantageous because of tendency to reduction in a production efficiency for 1,3-dimethyl-2-imidazolidinone while a residence time of more than 24 hour is disadvantageous because of tendency to reduction in a volumetric efficiency of a reactor. A pressure depends on factors such as a temperature and the amounts of starting materials; preferably 4 MPa to 30 MPa both inclusive. A pressure of less than 4 MPa is disadvantageous because of tendency to reduction in a production efficiency for 1,3-dimethyl-2-imidazolidinone while a pressure of more than 30 MPa is disadvantageous because of increase in a production cost of a reactor.

In the process of this invention, the amount of the second component supplied to the second reaction step is determined such that the total molar amount of the following i'") to iii'") is preferably at least two folds of the molar amount of ethylene oxide supplied to the first reaction step. More preferably, the amount of monomethylamine is determined such that the above molar ratio is 2 to 39 folds both inclusive. The molar ratio of less than two folds may be disadvantageous because of tendency to reduction in an yield of 1,3-dimethyl-2-imidazolidinone, while that of more than 39 folds may be disadvantageous because of reduction in a volumetric efficiency of a reactor, and increase in a cost for recovering unreacted monomethylamine, the carbon dioxide compound of monomethylamine and 1,3-dimethylurea:

i'") the total of the molar amount of monomethylamine fed from the first reaction step to the second reaction step, the molar amount of monomethylamine recovered and recycled and the molar amount of monomethylamine newly supplied;

ii'") the total of the molar amount of monomethylamine part in the carbon dioxide compound of monomethylamine fed from the first reaction step to the second reaction step, the molar amount of monomethylamine part in the carbon dioxide compound of monomethylamine recovered and recycled and the molar amount of monomethylamine in the carbon dioxide compound of monomethylamine newly supplied; and iii''') the total of the double of the molar amount of 1,3-dimethylurea fed from the first reaction step to the second reaction step, the double of the molar amount of 1,3-dimethylurea recovered and recycled and the double of the molar amount of 1,3-dimethylurea newly supplied.

In the process of this invention, carbon dioxide used in the second reaction step may be used as gaseous, liquid, solid or supercritical carbon dioxide. The amount of the second component supplied to the second reaction step is determined such that the total molar amount of the following iv''') to vi''') is preferably at least 1.5 folds, more preferably 4 to 100 folds both inclusive of the molar amount of ethylene oxide supplied. This molar ratio of less than 1.5 folds is disadvantageous because of tendency to reduction in an yield of 1,3-dimethyl-2-imidazolidinone, while the molar ratio of more than 100 folds may be disadvantageous because of tendency to reduction in a volumetric efficiency of the reactor:

iv''') the total of the molar amount of carbon dioxide fed from the first reaction step to the second reaction step, the molar amount of carbon dioxide recovered and recycled and the molar amount of carbon dioxide newly supplied;

v''') the total of the molar amount of carbon dioxide part in the carbon dioxide compound of monomethylamine fed from the first reaction step to the second reaction step, the molar amount of carbon dioxide part in the carbon dioxide compound of monomethylamine recovered and recycled and the molar amount of carbon dioxide part in the carbon dioxide compound of monomethylamine newly supplied; and vi''') the total of the molar amount of 1,3-dimethylurea fed from the first reaction step to the second reaction step, the molar amount of 1,3-dimethylurea recovered and recycled and the molar amount of 1,3-dimethylurea newly supplied.

In the second reaction step, water may be introduced via line L4. The amount of water supplied is determined such that the total of water fed from the first reaction step, water recovered and recycled in the second reaction step and water newly supplied is preferably 100 parts by weight or less, more preferably 50 parts by weight or less to one part by weight of ethylene oxide supplied to the first reaction step.

In the 1,3-dimethyl-2-imidazolidinone preparation step or the second reaction step, DMI is produced. The reaction mixture obtained in the 1,3-dimethyl-2-imidazolidinone preparation step or the second reaction step contains water; low-boiling amines which are amines having a boiling point higher than that of water and lower than that of DMI such as 2-(methylamino)ethanol, 1,3-dimethylpiperazine and N,N'-dimethylethylenediamine; high-boiling compounds which are compounds having a boiling point higher than that of DMI such as 1,3-dimethylurea, 1-methyl-2-imidazolidinone and N-methyldiethanolamine; ammonia and its carbon dioxide compounds, monomethylamine, dimethylamine, trimethylamine, and carbon dioxide compounds of these amines; and carbon dioxide, as byproducts or unreacted materials. Examples of a carbon dioxide compound of ammonia or an amine include carbamates, carbonates and hydrogencarbonates.

The reaction mixture in the 1,3-dimethyl-2-imidazolidinone preparation step or the second reaction step is fed to the first separation step (2) via line L6.

In the first separation step, the reaction mixture obtained in the 1,3-dimethyl-2-imidazolidinone preparation step or the second reaction step is separated into the first fraction containing monomethylamine, carbon dioxide and the carbon dioxide compound of monomethylamine as main components, and also containing water; and the second fraction containing DMI and the above high-boiling compounds as main components, and also containing water. The first fraction may be fed to the fourth separation step (5) via lines L7, L14, L16 and L19, while the second fraction may be fed to the second separation step (3) via lines L8, L10 and L13.

Separation in the first separation step is preferably conducted at a pressure lower than that in the 1,3-dimethyl-2-imidazolidinone preparation step or the second reaction step. Such a lower pressure may facilitate vaporization of low-boiling components such as monomethylamine and a part of water, which are fed to the fourth separation step.

The process of this invention may comprise an absorption step (10) between the first separation step and the fourth separation step. In such a case, the first fraction in the first separation step is fed to the absorption step via lines L7, L14 and L15.

In the absorption step, the first fraction in the first separation step is contacted with and absorbed in a solvent fed via line L17. The first fraction in the first separation step may be introduced to the absorption step as, for example, a gas, a liquid, a solution such as an aqueous solution or any mixture of these. Any solvent can be used as long as it is inert to reaction substrates in the 1,3-dimethyl-2-imidazolidinone preparation step, the first reaction step and the second reaction step. Examples of a solvent used generally include water, hydrocarbons, ethers, amides and circular ureas. Among these, water and DMI are preferable and water is more preferable. Water and DMI are preferable because they are a starting material or product in the 1,3-dimethyl-2-imidazolidinone preparation step or the second reaction step, eliminating an additional recovery step. These solvents may be used alone or in combination of two or more. Depending on a solvent used, the absorption may be conducted in a multiphase (two or more phase) system.

A part of carbon dioxide which is not absorbed in a solvent in the absorption step may be discharged outside of the system via line L20.

The absorption solution in the absorption step is supplied to the fourth separation step (5) via lines L18 and L19.

In the fourth separation step, ammonia, dimethylamine, trimethylamine, the carbon dioxide compound of ammonia, the carbon dioxide compound of dimethylamine, and the carbon dioxide compound of trimethylamine produced as byproducts in the 1,3-dimethyl-2-imidazolidinone preparation step or the second reaction step are removed into line L22 as the first fraction. Monomethylamine and its carbon dioxide compound are recovered as the second fraction from the bottom of the separator. When using the absorption step, a part of the solvent in the absorption step is recovered as the second fraction. The second fraction is recycled to the 1,3-dimethyl-2-imidazolidinone preparation step via lines L23 and L5, or to the first reaction step and/or the second reaction step. A part of the second fraction may be discarded while the remaining may be recycled to the 1,3-dimethyl-2-imidazolidinone preparation step or to the first reaction step and/or the second reaction step. The first fraction may be discarded or undergo a disproportionation reaction to provide monomethylamine and then recycled to the 1,3-dimethyl-2-imidazolidinone preparation step or the first reaction step and/or the second reaction step.

The fourth separation step is preferably conducted in the presence of carbon dioxide for improving a separation/recovery efficiency for monomethylamine and/or its carbon dioxide compound. Carbon dioxide may be used as any of gaseous, liquid, solid or supercritical carbon dioxide. Because, the reaction is conducted in the presence of carbon dioxide in the 1,3-dimethyl-2-imidazolidinone preparation step or the second reaction step, the separation in the fourth separation step can be conducted without feeding additional carbon dioxide. Alternatively, the first fraction in the first separation step or the absorption solution fed from the absorption step can be contacted with carbon dioxide supplied from line L21.

The fourth separation step may be conducted as a multistage process or combined with a distillation process. Such a multistage process or combination with a distillation process may improve a recovery efficiency for monomethylamine.

When the fourth separation step is conducted as a multistage process, the first fraction in the first separation step may be absorbed in water before being fed to a subsequent stage.

The second fraction containing DMI and the above high-boiling compounds as main components and also containing water in the first separation step is generally fed to the second separation step (3) via lines L8, L10 and L13.

The process of this invention may comprise a hydrolysis step (9) between the first separation step and the second separation step. In such a case, 1,3-dimethylurea can be hydrolyzed by feeding the second fraction in the first separation step to the hydrolysis step via lines L8 and L9, in which step the fraction is heated at 50° C. or higher. The hydrolysis-reaction mixture is separated into a first fraction containing, as main components, monomethylamine, carbon dioxide, and the carbon dioxide compound of monomethylamine prepared by hydrolysis and also containing water; and a second fraction containing DMI and the above high-boiling compounds as main components and also containing water. The first fraction is fed to the fourth separation step via lines L11, L14, L16 and L19. When using an absorption step, the first fraction is fed to the absorption step via lines L11, L14 and L15. The second fraction is fed to the second separation step via lines L12 and L13.

The mixture containing water and DMI fed to the second separation step via line L13 is separated into the first fraction containing water and low-boiling amines as main components and the second fraction containing DMI and the above high-boiling compounds as main components. The second fraction is fed to the third separation step (4) via line L24. The first fraction may be discarded, or recycled to the 1,3-dimethyl-2-imidazolidinone preparation step or the second reaction step via lines L25, L26, L30 and L5, when the content of 2-(methylamino)ethanol is low. When the content of 2-(methylamino)ethanol is significant, at least part of the first fraction may be recycled to the 1,3-dimethyl-2-imidazolidinone preparation step or the second reaction step via lines L25, L26, L30 and L5. Alternatively, the fifth separation step (11) may be added for heighten the content of 2-(methylamino)ethanol in the circulating liquid.

To the fifth separation step is fed the first fraction in the second separation step via lines L25 and L27. The fifth separation step separates the fraction into the first fraction containing water as a main component and the second fraction containing 2-(methylamino)ethanol as a main component. The second fraction is recycled to the 1,3-dimethyl-2-imidazolidinone preparation step or the second reaction step via lines L29, L30 and L5. In the fifth separation step, 2-(methylamino)ethanol may be separated for effectively recycling 2-(methylamino) ethanol contained in the first fraction in the second separation step to the 1,3-dimethyl-2-imidazolidinone preparation step or the second reaction step. The first fraction in the fifth separation step may be discarded, or at least part of the fraction may be recycled to the 1,3-dimethyl-2-imidazolidinone preparation step or the second reaction step.

The mixture containing DMI and the above high-boiling compounds fed to the third separation step (4) via line L24 is separated into a first fraction containing DMI as a main component and a second fraction containing the above high-boiling compounds as main components in the third separation step.

DMI as a desired product is obtained as the first fraction in the third separation step. A rectification step (12) may be added for providing DMI with a further improved purity. In such a case, the first fraction in the third separation step is fed to the rectification step via line L32 and rectified in the rectification step to provide DMI with a high purity.

At least part of the second fraction in the third separation step may be recycled to the 1,3-dimethyl-2-imidazolidinone preparation step or the second reaction step via lines L31, L33, L34 and L5. Circulation of the second fraction allows unreacted N-methyldiethanolamine to be recycled. Furthermore, 1,3-dimethylurea as a byproduct in the 1,3-dimethyl-2-imidazolidinone preparation step or the second reaction step may be circulated to allow 1,3-dimethylurea to be reacted with water in the reaction system and decomposed into monomethylamine, carbon dioxide and the carbon dioxide compound of monomethylamine. It can, therefore, reduce the amounts of monomethylamine and carbon dioxide newly supplied to the 1,3-dimethyl-2-imidazolidinone preparation step or the second reaction step.

The process of this invention may comprise the sixth separation step (13) In such a case, the second fraction in the third separation step is fed to the sixth separation step via lines L31 and L37. In the sixth separation step, the fraction is separated into a first fraction containing N-methyldiethanolamine and 1,3-dimethylurea as main components and a second fraction containing compounds with a higher boiling point than that of 1,3-dimethylurea such as 1-methyl-2-imidazolidinone as main components. At least part of the first fraction may be circulated into the 1,3-dimethyl-2-imidazolidinone preparation step or the second reaction step via lines L39, L34 and L5. The second fraction may be discarded. Alternatively, this fraction may undergo methylation to provide DMI and then fed to the third separation step. The sixth separation step can allow N-methyldiethanolamine and/or 1,3-dimethylurea to be effectively circulated into the 1,3-dimethyl-2-imidazolidinone preparation step or the second reaction step.

In the process of this invention, a reactor for the 1,3-dimethyl-2-imidazolidinone preparation step, the first reaction step and the second reaction step may be made of an appropriate known material, and a reactor whose inner wall is at least partly made of a metal and/or its oxide containing at least one selected from the group consisting of titanium and zirconium is preferable. Using such a reactor may allow DMIs to be prepared with a higher yield. Examples of such a reactor include those totally made of a metal containing titanium or zirconium; and those whose inner wall is at least partly coated with a metal or its oxide containing titanium or zirconium. Examples of a metal containing titanium or zirconium include industrial pure titanium in JIS Groups 1 to 4; anticorrosion titanium alloys such as Ti-0.15Pd, Ti-5Ta and Ti-0.3Mo-0.8Ni; α-type titanium alloys such as Ti-2.5Sn, Ti-5Al-2.5Sn, Ti-5Al-2.5Sn(ELI), Ti-2.5Cu, Ti-20-1N-5Fe, Ti-5Ni-0.5Ru, Ti-0.5Pd-3Co and Ti-5.5Al-3.5Sn-3Zr-1Nb-0.3Mo-0.3Si; near α-type titanium alloys such as Ti-8Al-1Mo-1V, Ti-2.25Al-11Sn-5Zr-1Mo-0.2Si, Ti-6Al-2Sn-4Zr-2Mo, Ti-5Al-5Sn-2Zr-2Mo-0.25Sn, Ti-6Al-2Nb-1Ta-0.8Mo, Ti-6Al-5Zr-0.5Mo-0.2Si and Ti-4.5Al-3V-2Fe-2Mo; α+β-type titanium alloys such as Ti-5Al-2Cr-1Fe, Ti-5Al-5Sn-5Zr-2Cr-1Fe, Ti-4Al-4Mn, Ti-3Al-2.5V, Ti-6Al-4V, Ti-6Al-4V(ELI), Ti-6Al-6V-2Sn, Ti-6Al-2Sn-4Zr-6Mo, Ti-7Al-4Mo, Ti-5Al-2Zr-4Mo-4Cr, Ti-6Al-1.7Fe-0.1Si, Ti-6.4Al-1.2Fe, Ti-15Zr-4Nb-2Ta-2Pd, Ti-6Al-7Nb and Ti-8Mn; β-type titanium alloys such as Ti-13V-11Cr-3Al, Ti-15Mo-5Zr, Ti-15Mo-0.2Pd, Ti-15V-3Cr-3Sn-3Al, Ti-20V-4Al-1Sn, Ti-22V-4Al and Ti-16V-4Sn-3Al-3Nb; near β-type titanium alloys such as Ti-10V-2Fe-3Al and Ti-9.5V-2.5Mo-3Al; zirconium alloys such as zircaloy-2, zircaloy-4, Zr-2.5Nb and ozenite. Among these metals, titanium-containing metals are preferable and industrial pure titanium or an anticorrosion titanium alloy is more preferable.

In the process of this invention, a separator in the first separation step may be made of an appropriate known material. In a preferable separator, the inner wall is at least partly made of (I) a metal and/or its oxide containing at least one selected from the group consisting of titanium and zirconium or (II) an inorganic glass. Use of such a separator is advantageous because it may prevent solid formation and line clogging. Examples of a separator include those entirely made of a metal containing titanium or zirconium; those whose inner wall is at least partially coated with a metal containing titanium or zirconium or its oxide; those entirely made of an inorganic glass; and those whose inner wall is coated with an inorganic glass.

Examples of a metal containing titanium or zirconium may be as described in the 1,3-dimethyl-2-imidazolidinone preparation step. Among these metals, a titanium-containing metal is preferable and industrial pure titanium or an anticorrosion titanium alloy is more preferable.

An inorganic glass in this invention means an inorganic material in a glass state, including element glasses, hydrogen-bonding glasses, oxide glasses, fluoride glasses, chloride glasses, sulfide glasses, carbonate glasses, nitrate glasses and sulfate glasses.

Among these, preferable glasses are oxide glasses such as silicate glasses, phosphate glasses and borate glasses. More preferable glasses are silicate glasses such as quartz glass; alkali-silicate glasses such as water glass; soda-lime glasses such as sheet glass and crown glass; potash-lime glasses such as Bohemian glass and crystal glass; lead glasses such as flint glass; barium glasses such as barium flint glass; and silicate glasses such as borosilicate glass. Further preferable glasses include silicate glass, soda-lime glass and soda-lime glass containing aluminum, magnesium or calcium ions as modification ions.

In the process of this invention, a hydrolysis reactor in the hydrolysis step may be made of an appropriate known material. Preferably is used a hydrolysis reactor, whose inner wall is at least partly made of (I) a metal and/or its oxide containing at least one selected from the group consisting of titanium and zirconium or (II) an inorganic glass. Use of such a hydrolysis reactor is advantageous because it may prevent solid formation and line clogging. Examples of such a hydrolysis reactor include those entirely made of a metal containing titanium or zirconium; those whose inner wall is at least partially coated with a metal containing titanium or zirconium or its oxide; those entirely made of an inorganic glass; and those whose inner wall is coated with an inorganic glass.

Examples of a metal containing titanium or zirconium may be as described in the 1,3-dimethyl-2-imidazolidinone preparation step. Among these metals, a titanium-containing metal is preferable and industrial pure titanium or an anticorrosion titanium alloy is more preferable.

Inorganic glasses which may be used are as described for the separator. Among these, preferable glasses are oxide glasses such as silicate glasses, phosphate glasses and borate glasses. More preferable glasses are silicate glasses such as quartz glass; alkali-silicate glasses such as water glass; soda-lime glasses such as sheet glass and crown glass; potash-lime glasses such as Bohemian glass and crystal glass; lead glasses such as flint glass; barium glasses such as barium flint glass; and silicate glasses such as borosilicate glass. Further preferable glasses include silicate glass, soda-lime glass and soda-lime glass containing aluminum, magnesium or calcium ions as modification ions.

A style of a unit operation such as a reaction and separation in the process of this invention may be, but not limited to, a batch, semi-batch or continuous system.

The process of this invention allows byproducts to be effectively processed and DMI to be prepared with a higher efficiency.

This invention will be specifically described with reference to, but not limited to, examples. In the following examples, a fraction in a separation step or an absorption liquid in an absorption step are indicated, for instance, as follows: "the first fraction/the first separation step", "the second fraction/the first separation step", and "the absorption liquid/the absorption step."

EXAMPLE 1

In an autoclave with an inner volume of 400 cc whose lid, stirring rod and stirring blade were made of industrial pure titanium of JIS Group 2 and whose body was lined with industrial pure titanium of JIS Group 2 were charged 111.4 g of methylamine methylcarbamate (1050 mmol), 32.4 g of ion-exchange water (1800 mmol). The gases phase was replaced with nitrogen and then 13.2 g of ethylene oxide (300 mmol) and 33.0 g of carbon dioxide (750 mmol) were charged. The autoclave was externally heated with stirring for reacting the mixture at an internal temperature of 100° C. for 3 hours. Then, the internal temperature was raised to 200° C. and the mixture was reacted at the same temperature for 7 hours, during which the maximum pressure was 9.2 MPa.

After cooling the autoclave to an ambient temperature, the reaction mixture was opened to the atmospheric pressure. The reaction mixture was collected for analyzing by gas chromatography. An yield of DMI based on ethylene oxide was 46%.

EXAMPLE 2

[1,3-dimethyl-2-imidazolidinone Preparation Step (1st Time)]

In the autoclave described in Example 1 were charged the materials as described in Example 1. The autoclave was externally heated with stirring and the mixture was reacted at an internal temperature of 220° C. for 4 hours, during which the pressure was 11.0 MPa.

The autoclave was cooled to an ambient temperature and opened to the atmospheric pressure to give 158.3 of the reaction mixture.

The collected reaction mixture was analyzed by gas chromatography and Karl Fischer method. An yield of DMI based on ethylene oxide was 57%. The reaction mixture contained 0.44 g of ammonia and ammonia part in its carbon dioxide compound (hereinafter, collectively referred to as "ammonia component"); 36.8 g of monomethylamine and monomethylamine part in its carbon dioxide compound (hereinafter, collectively referred to as "monomethylamine component"); 1.12 g of dimethylamine and dimethylamine part of its carbon dioxide compound (hereinafter, collectively referred to as "dimethylamine component"); 0.11 g of trimethylamine and trimethylamine part in its carbon dioxide compound (hereinafter, collectively referred to as "trimethylamine component"); 19.4 g of 1,3-dimethyl-2-imidazolidinone; 0.20 g of 2-(methylamino)ethanol and 2-(methylamino)ethanol part in its carbon dioxide compound (hereinafter, collectively referred to as "2-(methylamino)ethanol component"); 0.41 g of 1,3-dimethylpiperazine; 0.20 g of N,N'-dimethylethylenediamine and N,N'-dimethylethylenediamine part in its carbon dioxide compound (hereinafter, collectively referred to as "N,N'-dimethylethylenediamine component"); 0.44 g of N,N-dimethylethanolamine; 1.05 g of 1-methyl-2-imidazolidinone; 2.57 g of N-methyldiethanolamine; 22.5 g of 1,3-dimethylurea; 43.9 g of water; and 27.4 g of carbon dioxide, carbon dioxide part of carbon dioxide compound of ammonia and carbon dioxide part of carbon dioxide compound of the above amines (monomethylamine, dimethylamine, trimethylamine, 2-(methylamino)ethanol and N,N'-dimethylethylenediamine) (hereinafter, collectively referred to as "carbon dioxide component").

Comparative Example 1

In the autoclave described in Example 1 were charged 88.6 g of methylamine methylcarbamate (835 mmol) and 52.2 g of ion-exchange water (2896 mmol). After the gaseous phase was replaced with nitrogen, 26.4 g of ethylene oxide (600 mmol) and 2.2 g of carbon dioxide (52 mmol). The autoclave was externally heated with stirring and the mixture was reacted at an internal temperature of 100° C. for 3 hours. The mixture was further heated to an internal temperature of 220° C., and reacted at the same temperature for 4 hours, during which the pressure was 3.3 MPa. The reaction mixture was collected and analyzed by gas chromatography as described in Example 1. An yield of DMI based on ethylene oxide was 16%.

EXAMPLE 3

[The First Separation Step]

To a three-necked borosilicate glass flask with an inner volume of 500 cc was placed 157.5 g of the reaction mixture collected in the 1,3-dimethyl-2-imidazolidinone preparation step (1st time) in Example 2. Under an atmospheric pressure, it was purified by simple distillation at an internal temperature of 80 to 117° C. to obtain 73.0 g of a fraction (the first fraction/the first separation step) from a distillation column. The first fraction/the first separation step was analyzed by gas chromatography and Karl Fischer method. The mixture contained 0.42 g of the ammonia component, 34.9 g of the monomethylamine component, 1.1 g of the dimethylamine component, 0.05 g of the trimethylamine component, 18.6 g of the carbon dioxide component and 17.6 g of water.

The residue after simple distillation (the second fraction/the first separation step) was analyzed by gas chromatography and Karl Fischer method. The residue contained 18.8 g of 1,3-dimethyl-2-imidazolidinone, 22.0 g of 1,3-dimethylurea, 25.3 g of water, 0.20 g of 2-(methylamino) ethanol and 1.03 g of 1-methyl-2-imidazolidinone.

[The Second Separation Step]

The second fraction/the first separation step was distilled under a reduced pressure at 64 to 66° C./230 torr (31 kPa) to collect 27.0 g of a fraction containing water (the first fraction/the second separation step). The fraction was analyzed by gas chromatography and contained 0.27 g of 1,3-dimethylpiperazine, 0.19 g of N,N'-dimethylethylenediamine, 0.38 g of N,N-dimethylaminoethanol and 0.19 g of 2-(methylamino) ethanol. The residue (the second fraction/the second separation step) was 43.8 g, containing 18.3 g of 1,3-dimethyl-2-imidazolidinone, 21.5 g of 1,3-dimethylurea and 2.5 g of N-methyldiethanolamine.

[The Third Separation Step]

The residue collected from the flask in the second separation step (the second fraction/the second separation step) was distilled under a pressure at 105 to 109° C./19.5 torr (2.5 kPa) to collect 16.8 g of a fraction containing 1,3-dimethyl-2-imidazolidinone with a purity of 99%.

[The Fourth Separation Step (Stage 1)]

The fraction collected in the first separation step (the first fraction/the first separation step) was placed in a three-necked flask with an inner volume of 200 mL. The flask was externally cooled by ice while 30 g of dry ice was slowly added until the system was saturated with carbon dioxide. Then, the top of the three-necked flask was equipped with a condenser and a trap via glass tubes, and the trap was cooled by ice-water.

The three-necked flask was immersed in an oil bath at 120° C. The mixture was refluxed by heating for 1 hour during which the maximum internal temperature of the flask was 93° C. After cooling to room temperature, 52.1 g of an aqueous solution in the flask (the second fraction/the fourth separation step (stage 1)) was collected and analyzed by gas chromatography and Karl Fischer method. The solution contained 26.3 g of the monomethylamine component, 0.0082 g of the ammonia component, 0.25 g of the dimethylamine component, 13.9 g of the carbon dioxide component and 11.3 g of water without a detectable level of the trimethylamine component.

[The Fourth Separation Step (Stage 2)]

In a 50 mL three-necked flask was placed the first fraction/the fourth separation step (stage 1) collected in the trap containing 7.8 g of the monomethylamine component, 0.39 g of the ammonia component, 0.76 g of the dimethylamine component and 0.005 g of the trimethylamine component. While externally cooling the flask with ice, 20 g of dry ice was slowly added until the system was saturated with carbon dioxide. Then, the mixture was refluxed by heating for 1 hour using the apparatus as described for the fourth separation step (stage 1), during which the maximum internal temperature in the flask was 93° C. After cooling to room temperature, 13.7 g of a solution in the flask (the second fraction/the fourth separation step (stage 2)) was collected and analyzed by gas chromatography and Karl Fischer method. The solution contained 6.1 g of the monomethylamine component, 0.0058 g of the ammonia component, 0.19 g of the dimethylamine component, 3.3 g of the carbon dioxide component and 4.1 g of water without a detectable level of the trimethylamine component.

[1,3-dimethyl-2-imidazolidinone Preparation Step (2nd Time)]

In the autoclave as described in the 1,3-dimethyl-2-imidazolidinone preparation step (1st time) was charged 63.8 g of the aqueous solution (31.5 g of the monomethylamine component, 16.7 g of the carbon dioxide component and 14.8 g of water) containing monomethylamine (the second fraction/the fourth separation step (stage 1) and, the second fraction/the fourth separation step (stage 2)) collected in the fourth separation step (stage 1) and the fourth separation step (stage 2) respectively, and then charged 17.6 g of ion-exchange water and 57.6 g of methylamine methylcarbamate. After replacing the gaseous phase with nitrogen, 13.2 g of ethylene oxide (300 mmol) and 38.7 g of carbon dioxide were charged. That is, the materials were charged such that the total of the molar amount of monomethylamine and the molar amount of the monomethylamine part in the carbon dioxide compound of monomethylamine, the total of the molar amount of carbon dioxide and the molar amount of the carbon dioxide part in the carbon dioxide compound of monomethylamine, and the molar amount of water was equal to those charged in the 1,3-dimethyl-2-imidazolidinone preparation step (1st time) respectively. The mixture was reacted at an internal temperature of 220° C. for 4 hours as described for the 1,3-dimethyl-2-imidazolidinone preparation step (1st time).

The reaction mixture was collected and analyzed as described for the 1,3-dimethyl-2-imidazolidinone preparation step (1st time). An yield of DMI based on ethylene oxide was 56%. The reaction mixture contained 1.1 g of 1-methyl-2-imidazolidinone and 0.45 g of the ammonia component.

Comparative Example 2

In the 1,3-dimethyl-2-imidazolidinone preparation step (2nd time) in Example 3, 72.0 g of the first fraction/the first separation step (34.4 g of the monomethylamine component, 0.41 g of the ammonia component, 1.05 g of the dimethylamine component, 18.3 g of the carbon dioxide component and 17.4 g of water) was charged in place of the second fraction/the fourth separation step (stage 1) and the second fraction/the fourth separation step (stage 2). Furthermore, materials were charged so that the amounts of monomethylamine component, the carbon dioxide component, water and ethylene oxide were equal to those charged in the 1,3-dimethyl-2-imidazolidinone preparation step (2nd time) in Example 3. Reaction and analysis were conducted as described for the 1,3-dimethyl-2-imidazolidinone preparation step (2nd time) in Example 3. An yield of DMI based on ethylene oxide was 50%. The reaction mixture contained 2.1 g of 1-methyl-2-imidazolidinone and 0.86 g of the ammonia component.

As described above, monomethylamine collected in the fourth separation step may be circulated for recycling to prevent increase of byproducts and provide DMI with a higher yield.

EXAMPLE 4

[The First Reaction Step (1st Time)]

In the autoclave as described in Example 1 was charged 37.8 g of ion-exchange water (2100 mmol). After replacing the gaseous phase with nitrogen, 93.2 g of monomethylamine (3000 mmol) and 23.8 g of carbon dioxide (540 mmol) were charged. The autoclave was externally heated to an internal temperature of 100° C. with stirring. After the internal temperature reached 100° C., 13.2 g of ethylene oxide (300 mmol) was added, and the mixture was heated at an internal temperature of 100° C. for 1 hour.

[The Seventh Separation Step]

The autoclave in the first reaction step (1st time) was cooled to 70° C., and was gradually opened to the atmospheric pressure while monomethylamine was collected from the gaseous phase into a pressure bottle with an inner volume of 200 cc cooled to −78° C. (the first fraction/the seventh separation step) to provide 42.7 g of monomethylamine.

[The Second Reaction Step (1st Time)]

Gas chromatography for the residual reaction mixture in the autoclave in the seventh separation step (the second fraction/the seventh separation step) indicated that no ethylene oxide existed and that yields for 2-(methylamino) ethanol and N-methyldiethanolamine based on ethylene oxide were 85% and 15%, respectively. The reaction mixture contained 19.2 of the 2-(methylamino)ethanol component, 2.68 g of the N-methyldiethanolamine component, 41.8 g of the monomethylamine component, 37.8 g of water and 23.8 g of the carbon dioxide component.

Then, 16.4 g of ion-exchange water (913 mmol), 14.3 g of monomethylamine (461 mmol) and 55.6 g of carbon dioxide (1263 mmol) were charged in the autoclave containing the reaction mixture (the second fraction/the seventh separation step) comprising 19.0 g of the 2-(methylamino)ethanol component, 2.67 g of the N-methyldiethanolamine, 41.6 g of the monomethylamine component, 23.6 g of the carbon dioxide component and 37.6 g of water. The mixture was reacted at an internal temperature of 200° C. for 5 hours, during which the maximum pressure was 8.3 MPa.

After cooling the autoclave to room temperature, it was opened to the atmospheric pressure to collect 176.2 g of the reaction mixture.

The reaction mixture was analyzed by gas chromatography and Karl Fischer method, indicating that an yield for 1,3-dimethyl-2-imidazolidinone was 76% based on ethylene oxide. The reaction mixture contained 0.35 g of the ammonia component, 32.1 g of the monomethylamine component, 0.88 g of the dimethylamine component, 0.11 g of the trimethylamine component, 26.0 g of 1,3-dimethyl-2-imidazolidinone, 0.64 g of the 2-(methylamino)ethanol component, 0.77 g of 1,3-dimethylpiperazine, 0.69 g of the N,N'-dimethylethylenediamine component, 0.42 g of N,N-dimethylethanolamine, 0.42 g of 1-methyl-2-imidazolidinone, 1.34 g of N-methyldiethanolamine, 20.3 g of 1,3-dimethylurea, 67.1 g of water and 24.3 g of the carbon dioxide component.

[The First Separation Step and an Absorption Step]

In a borosilicate glass three-necked flask with an inner volume of 500 cc was placed 174.4 g of the reaction mixture collected in the second reaction step (1st time). The mixture was simply distilled under an ambient pressure at an internal temperature of 80 to 117° C. while a fraction from a distillation column was contacted with and absorbed in 10 g of ion-exchange water in a flask with an inner volume of 200 cc to obtain 86.4 g of an aqueous solution containing the fraction. The aqueous solution (absorption solution/absorption step) was analyzed by gas chromatography and Karl Fischer method. It contained 0.34 g of the ammonia component, 31.5 g of the monomethylamine component, 0.86 g of the dimethylamine component, 0.11 g of the trimethylamine component, 16.7 g of the carbon dioxide component and 36.9 g of water.

The residue after the simple distillation (the second fraction/the first separation step) was also analyzed by gas chromatography and Karl Fischer method. The residue contained 25.2 g of 1,3-dimethyl-2-imidazolidinone, 19.9 g of 1,3-dimethylurea, 38.8 g of water, 0.63 g of 2-(methylamino)ethanol and 0.42 g of 1-methyl-2-imidazolidinone.

[The Second Separation Step]

The second fraction/the first separation step was distilled in vacuo at 64 to 66° C./230 torr (31 kPa) to collect 40.5 g of a water-containing fraction (the first fraction/the second separation step). The fraction was analyzed by gas chromatography, indicating that it contained 0.51 g of 1,3-dimethylpiperazine, 0.66 g of N,N'-dimethylethylenediamine, 0.36 g of N,N-dimethylaminoethanol and 0.61 g of 2-(methylamino) ethanol. The distillation left 46.2 g of a residue (the second fraction/the second separation step) containing 24.5 g of 1,3-dimethyl-2-imidazolidinone, 19.5 g of 1,3-dimethylurea and 1.3 g of N-methyldiethanolamine.

[The Third Separation Step]

The residue collected from the flask in the second separation step (the second fraction/the second separation step) was distilled in vacuo at 105 to 109° C./19.5 torr (2.5 kPa) to collect 22.6 g of 1,3-dimethyl-2-imidazolidinone with a purity of 99% as a distillate (the first fraction/the third separation step).

[The Fourth Separation Step (Stage 1)]

In a three-necked flask with an inner volume of 200 mL was placed the aqueous solution containing the fraction collected in the first separation step (absorption solution/absorption step). While externally cooling the flask with ice, 30 g of dry ice was slowly added until the system was saturated with carbon dioxide. Then, the top of the three-necked flask was equipped with a trap containing 10 g of ion-exchange water via a glass tube, and the trap was cooled by ice-water.

The three-necked flask was immersed in an oil bath at 120° C., and the mixture was refluxed by heating for 1 hour during which the maximum internal temperature of the flask was 93° C. After cooling to room temperature, 54.3 g of an aqueous solution in the flask (the second fraction/the fourth separation step (stage 1)) was collected and analyzed by gas chromatography and Karl Fischer method. The solution contained 23.7 g of the monomethylamine component, 0.0068 g of the ammonia component, 0.20 g of the dimethylamine component, 12.5 g of the carbon dioxide component and 17.3 g of water without a detectable level of the trimethylamine component.

[The Fourth Separation Step (Stage 2)]

In a 200 mL three-necked flask was placed the aqueous solution of the first fraction/the fourth separation step (stage 1) collected in the trap. This solution contained 7.1 g of the monomethylamine component, 0.32 g of the ammonia component, 0.63 g of the dimethylamine component and 0.072 g of the trimethylamine component. While externally cooling the flask with ice, 20 g of dry ice was slowly added until the system was saturated with carbon dioxide. Then, the mixture was refluxed by heating for 1 hour using the apparatus as described for the fourth separation step (stage 1), during which the maximum internal temperature in the flask was 93° C. After cooling to room temperature, 21.8 g of a solution in the flask (the second fraction/the fourth separation step (stage 2)) was collected and analyzed by gas chromatography and Karl Fischer method. The solution contained 5.6 g of the monomethylamine component, 0.0049 g of the ammonia component, 0.16 g of the dimethylamine component, 3.0 g of the carbon dioxide component and 12.9 g of water without a detectable level of the trimethylamine component.

An aqueous solution containing 74.0 g of monomethylamine (the second fraction/the fourth separation step) was obtained as the total of the second fraction/the fourth separation step (stage 2) and the second fraction/the fourth separation step (stage 1).

[The First Reaction Step (2nd time)]

In the autoclave as described in the first reaction step (1st time) was charged 69.5 g of the aqueous solution containing monomethylamine (the second fraction/the fourth separation step) (26.9 g of the monomethylamine component, 14.2 g of the carbon dioxide component and 27.5 g of water) collected in the fourth separation step (stage 1) and the fourth separation step (stage 2), and then 10.3 g of ion-exchange water. After replacing the gaseous phase with nitrogen, 42.5 g of the first fraction/the seventh separation step collected in the seventh separation step, 23.8 g of monomethylamine and 9.5 g of carbon dioxide were charged. That is, the materials were charged such that the total of the molar amount of monomethylamine and the molar amount of the monomethylamine part in the carbon dioxide compound of monomethylamine, the total of the molar amount of carbon dioxide and the molar amount of the carbon dioxide part in the carbon dioxide compound of monomethylamine, and the molar amount of water was equal to those charged in the first reaction step (1st time). With stirring, the autoclave was externally heated to an internal temperature of 100° C. After the internal temperature reached 100° C., 13.2 g of ethylene oxide (0.3 mol) was added and heating was continued at an internal temperature of 100° C. for 1 hour.

The reaction mixture was collected and analyzed by gas chromatography as described in the second reaction step (1st time), indicating that an conversion ratio of ethylene oxide was 100% and yields of 2-(methylamino)ethanol and N-methyldiethanolamine were 85% and 15%, respectively, based on ethylene oxide newly charged in the first reaction step (2nd time).

[The Second Reaction Step (2nd Time)]

To the reaction mixture left in the autoclave in the first reaction step (2nd time) containing 18.9 g of the 2-(methylamino)ethanol component, 2.65 g of N-methyldiethanolamine, 41.7 g of the monomethylamine component, 23.8 g of the carbon dioxide component and 37.8 g of water were added 4.5 g of the monomethylamine-containing aqueous solution comprising 1.76 g of the monomethylamine component, 0.93 g of the carbon dioxide component and 1.80 g of water (the second fraction/the fourth separation step) collected in the fourth separation step (stage 1) and the fourth separation step (stage 2); 21.0 g of the residue containing 17.8 g of 1,3-dimethylurea in the third separation step (the second fraction/the third separation step); and then 18.3 g of ion-exchange water. After replacing the gaseous phase with nitrogen, 45.8 g of carbon dioxide was charged. That is, the following a) to c) were charged in an equal amount to that in the second reaction step (1st time), respectively:

a) the total of the molar amount of monomethylamine, the molar amount of the monomethylamine part in the carbon dioxide compound of monomethylamine and the double of the molar amount of 1,3-dimethylurea, b) the total of the molar amount of carbon dioxide, the molar amount of the carbon dioxide part in the carbon dioxide compound of monomethylamine, the molar amount of the carbon dioxide part in the carbon dioxide compound of 2-(methylamino)ethanol and the molar amount of 1,3-dimethylurea, and c) a difference between the molar amount of water and the molar amount of 1,3-dimethylurea.

The mixture was reacted at an internal temperature of 200° C. for 5 hours as described in the second reaction step (1st time).

The reaction mixture was collected and analyzed as described in the second reaction step (1st time), indicating that an yield of 1,3-dimethyl-2-imidazolidinone was 76% based on ethylene oxide newly charged in the first reaction step (2nd time).

Industrial Applicability

As described above, the process of this invention is suitable for industrially preparing a 1,3-dialkyl-2-imidazolidinones using an industrially readily available alkylene oxide as a starting material. In particular, in a process for preparing 1,3-dimethyl-2-imidazolidinone, 1,3-dimethyl-2-imidazolidinone can be prepared with a higher efficiency while effectively separating and processing byproducts such as N-methyldiethanolamine, ammonia, dimethylamine, trimethylamine, 1-methyl-2-imidazolidinone and 1,3-dimethylurea.

What is claimed is:

1. A process for preparing a 1,3-dimethyl-2-imidazolidinone by using ethylene oxide as a first component, using at least one selected from the group consisting of the following components (D), (E) and (F) as a second component:

component (D): carbon dioxide and monomethylamine;

component (E): a carbon dioxide compound of monomethylamine and component (F): 1,3-dimethylurea, wherein the process comprises:

(1) a 1,3-dimethyl-2-imidazolidinone preparation step of preparing 1,3-dimethyl-2-imidazolidinone by heating said first component and said second component at 50° C. or higher, characterized in that the reaction is conducted under a pressure of 4 MPa or higher and that 1,3-dimethyl-2-imidazolidinone is prepared via corresponding N-alkylmonoethanolamine and N-alkyldiethanolamine as intermediates, and the total molar amount of a molar feed amount of the monomethylamine included in the component (D), a molar feed amount of the monomethylamine part of the carbon dioxide compound of monomethylamine, said compound being component (E), and the double of a molar feed amount of the 1,3-dimethylurea, said 1,3-dimethylurea being component (F), is at least three folds of a molar feed amount of said ethylene oxide and characterized in that the total molar amount of a molar feed amount of the carbon dioxide included in the component (D), a molar feed amount of the carbon dioxide part of the carbon dioxide compound of monomethylamine, said compound being the component (E), and a molar feed amount of the 1,3-dimethylurea, said 1,3-dialkylurea being the component (F), is at least one and a half folds of a molar feed amount of said ethylene oxide and the process further comprises:

(2) a first separation step of separating the reaction mixture obtained in the 1,3-dimethyl-2-imidazolidinone preparation step into a first fraction containing monomethylamine, carbon dioxide and a carbon dioxide compound of monomethylamine as main components, and also containing water; and a second fraction containing 1,3-dimethyl-2-imidazolidinone and high-boiling compounds with a higher boiling point than that of 1,3-dimethyl-2-imidazolidinone as main components, and also containing water;

(3) a second separation step of separating at least part of the second fraction in the first separation step into a first fraction containing water and low-boiling amines with a boiling point higher than that of water and lower than that of 1,3-dimethyl-2-imidazolidinone as main components; and a second fraction containing 1,3-dimethyl-2-imidazolidinone and said high-boiling compounds as main components;

(4) a third separation step of separating the second fraction in the second separation step into a first fraction containing 1,3-dimethyl-2-imidazolidinone as a main component; and a second fraction containing said high-boiling compounds as main components; and (5) a fourth separation step of separating the first fraction in the first separation step into a first fraction containing ammonia, dimethylamine, trimethylamine, a carbon dioxide compound of ammonia, a carbon dioxide compound of dimethylamine and a carbon dioxide compound of trimethylamine as main components, and also containing water; and a second fraction containing monomethylamine and a carbon dioxide compound of monomethylamine as main components, and also containing water, where at least part of the second fraction in the fourth separation step is supplied in the 1,3-dimethyl-2-imidazolidinone preparation step.

2. The process as claimed in claim 1, characterized in that the 1,3-dimethyl-2-imidazolidinone preparation step is carried out by:

(6) a first reaction step of heating ethylene oxide and at least one selected from the group consisting of the components (D), (E) and (F) at 50° C. or higher to prepare N-methyldiethanolamine and 2-(methylamino)ethanol; and (7) a second reaction step of heating N-methyldiethanolamine and 2-(methylamino)ethanol prepared in the first reaction step with at least one selected from the group consisting of the components (D), (E) and (F) at 100° C. or higher to prepare 1,3-dimethyl-2-imidazolidinone, and the second fraction in the fourth separation step is supplied in said first reaction step and/or said second reaction step.

3. The process as claimed in claim 2, characterized in that in the fourth separation step, at least part of the first fraction in the first separation step is contacted with carbon dioxide, heated at 50° C. or higher, and separated by vapor-liquid separation to remove the first fraction in the fourth separation step into the gaseous phase and obtain the second fraction in the fourth separation step from the liquid phase.

4. The process as claimed in claim 1, characterized in that in the fourth separation step, at least part of the first fraction in the first separation step is contacted with carbon dioxide, heated at 50° C. or higher, and separated by vapor-liquid separation to remove the first fraction in the fourth separation step into the gaseous phase and obtain the second fraction in the fourth separation step from the liquid phase.

5. A process for preparing a 1,3-dimethyl-2-imidazolidinone by using ethylene oxide as a first component, using at least one selected from the group consisting of the following components (D), (E) and (F) as a second component:

component (D): carbon dioxide and monomethylamine;

component (E): a carbon dioxide compound of monomethylamine and component (F): 1,3-dimethylurea, wherein the process comprises:

(1) a 1,3-dimethyl-2-imidazolidinone preparation step of preparing 1,3-dimethyl-2-imidazolidinone by heating said first component and said second component at 50° C. or higher, characterized in that the 1,3-dimethyl-2-imidazolidinone is prepared via corresponding N-alkylmonoethanolamine and N-alkyldiethanolamine as intermediates, and the total molar amount of a molar feed amount of the monomethylamine included in the component (D), a molar feed amount of the monomethylamine part of the carbon dioxide compound of monomethylamine, said compound being component (E), and the double of a molar feed amount of the 1,3-dimethylurea, said 1,3-dimethylurea being component (F), is at least three folds of a molar feed amount of said ethylene oxide and characterized in that the total molar amount of a molar feed amount of the carbon dioxide included in the component (D), a molar feed amount of the carbon dioxide part of the carbon dioxide compound of monomethylamine, said compound being the component (E), and a molar feed amount of the 1,3-dimethylurea, said 1,3-dialkylurea being the component (F), is at least one and a half folds of a molar feed amount of said ethylene oxide and the process further comprises:

(2) a first separation step of separating the reaction mixture obtained in the 1,3-dimethyl-2-imidazolidinone preparation step into a first fraction containing monomethylamine, carbon dioxide and a carbon dioxide compound of monomethylamine as main components, and also containing water; and a second fraction containing 1,3-dimethyl-2-imidazolidinone and high-boiling compounds with a higher boiling point than that of 1,3-dimethyl-2-imidazolidinone as main components, and also containing water;

(3) a second separation step of separating at least part of the second fraction in the first separation step into a first fraction containing water and low-boiling amines with a boiling point higher than that of water and lower than that of 1,3-dimethyl-2-imidazolidinone as main components; and a second fraction containing 1,3-dimethyl-2-imidazolidinone and said high-boiling compounds as main components;

(4) a third separation step of separating the second fraction in the second separation step into a first fraction containing 1,3-dimethyl-2-imidazolidinone as a main component; and a second fraction containing said high-boiling compounds as main components; and (5) a fourth separation step of separating the first fraction in the first separation step into a first fraction containing ammonia, dimethylamine, trimethylamine, a carbon dioxide compound of ammonia, a carbon dioxide compound of dimethylamine and a carbon dioxide compound of trimethylamine as main components, and also containing water; and a second fraction containing monomethylamine and a carbon dioxide compound of monomethylamine as main components, and also containing water, where at least part of the second fraction in the fourth separation step is supplied in the 1,3-dimethyl-2-imidazolidinone preparation step.

6. The process as claimed in claim 5, characterized in that the 1,3-dimethyl-2-imidazolidinone preparation step is carried out by:

(6) a first reaction step of heating ethylene oxide and at least one selected from the group consisting of the components (D), (E) and (F) at 50° C. or higher to prepare N-methyldiethanolamine and 2-(methylamino)ethanol; and (7) a second reaction step of heating N-methyldiethanolamine and 2-(methylamino)ethanol prepared in the first reaction step with at least one selected from the group consisting of the components (D), (E) and (F) at 100° C. or higher to prepare 1,3-dimethyl-2-imidazolidinone, and the second fraction in the fourth separation step is supplied in said first reaction step and/or said second reaction step.

7. The process as claimed in claim 6, characterized in that in the fourth separation step, at least part of the first fraction in the first separation step is contacted with carbon dioxide, heated at 50° C. or higher, and separated by vapor-liquid separation to remove the first fraction in the fourth separation step into the gaseous phase and obtain the second fraction in the fourth separation step from the liquid phase.

8. The process as claimed in claim 5, characterized in that in the fourth separation step, at least part of the first fraction in the first separation step is contacted with carbon dioxide, heated at 50° C. or higher, and separated by vapor-liquid separation to remove the first fraction in the fourth separation step into the gaseous phase and obtain the second fraction in the fourth separation step from the liquid phase.

9. A process for preparing a 1,3-dimethyl-2-imidazolidinone by using ethylene oxide as a first component, using at least one selected from the group consisting of the following components (D), (E) and (F) as a second component:

component (D): carbon dioxide and monomethylamine;

component (E): a carbon dioxide compound of monomethylamine; and component (F): 1,3-dimethylurea, wherein the process comprises:

(1) a 1,3-dimethyl-2-imidazolidinone preparation step of preparing 1,3-dimethyl-2-imidazolidinone by heating said first component and said second component at 50° C. or higher, characterized in that the reaction is conducted under a pressure of 4 MPa or higher and that 1,3-dimethyl-2-imidazolidinone is prepared via corresponding N-alkylmonoethanolamine and N-alkyldiethanolamine as intermediates, and the total molar amount of a molar feed amount of the monomethylamine included in the component (D), a molar feed amount of the monomethylamine part of the carbon dioxide compound of monomethylamine, said compound being component (E), and the double of a molar feed amount of the 1,3-dimethylurea, said 1,3-dimethylurea being component (F), is at least three folds of a molar feed amount of said ethylene oxide and the process further comprises:

(2) a first separation step of separating the reaction mixture obtained in the 1,3-dimethyl-2-imidazolidinone preparation step into a first fraction containing monomethylamine, carbon dioxide and a carbon dioxide compound of monomethylamine as main components, and also containing water; and a second fraction containing 1,3-dimethyl-2-imidazolidinone and high-boiling compounds with a higher boiling point than that of 1,3-dimethyl-2-imidazolidinone as main components, and also containing water;

(3) a second separation step of separating at least part of the second fraction in the first separation step into a first fraction containing water and low-boiling amines with a boiling point higher than that of water and lower than that of 1,3-dimethyl-2-imidazolidinone as main components; and a second fraction containing 1,3-dimethyl-2-imidazolidinone and said high-boiling compounds as main components;

(4) a third separation step of separating the second fraction in the second separation step into a first fraction containing 1,3-dimethyl-2-imidazolidinone as a main component; and a second fraction containing said high-boiling compounds as main components; and (5) a fourth separation step of separating the first fraction in the first separation step into a first fraction containing ammonia, dimethylamine, trimethylamine, a carbon dioxide compound of ammonia, a carbon dioxide compound of dimethylamine and a carbon dioxide compound of trimethylamine as main components, and also containing water; and a second fraction containing monomethylamine and a carbon dioxide compound of monomethylamine as main components, and also containing water, where at least part of the second fraction in the fourth separation step is supplied in the 1,3-dimethyl-2-imidazolidinone preparation step.

10. The process as claimed in claim 9, characterized in that the 1,3-dimethyl-2-imidazolidinone preparation step is carried out by:

(6) a first reaction step of heating ethylene oxide and at least one selected from the group consisting of the components (D), (E) and (F) at 50° C. or higher to prepare N-methyldiethanolamine and 2-(methylamino)ethanol; and (7) a second reaction step of heating N-methyldiethanolamine and 2-(methylamino)ethanol prepared in the first reaction step with at least one selected from the group consisting of the components (D), (E) and (F) at 100° C. or higher to prepare 1,3-dimethyl-2-imidazolidinone, and the second fraction in the fourth separation step is supplied in said first reaction step and/or said second reaction step.

11. The process as claimed in claim 10, characterized in that in the fourth separation step, at least part of the first fraction in the first separation step is contacted with carbon dioxide, heated at 50° C. or higher, and separated by vapor-liquid separation to remove the first fraction in the fourth separation step into the gaseous phase and obtain the second fraction in the fourth separation step from the liquid phase.

12. The process as claimed in claim 9, characterized in that in the fourth separation step, at least part of the first fraction in the first separation step is contacted with carbon dioxide, heated at 50° C. or higher, and separated by vapor-liquid separation to remove the first fraction in the fourth separation step into the gaseous phase and obtain the second fraction in the fourth separation step from the liquid phase.

13. A process for preparing a 1,3-dimethyl-2-imidazolidinone by using ethylene oxide as a first component, using at least one selected from the group consisting of the following components (D), (E) and (F) as a second component:

component (D): carbon dioxide and monomethylamine;

component (E): a carbon dioxide compound of monomethylamine; and component (F): 1,3-dimethylurea, wherein the process comprises:

(1) a 1,3-dimethyl-2-imidazolidinone preparation step of preparing 1,3-dimethyl-2-imidazolidinone by heating said first component and said second component at 50° C. or higher, characterized in that the 1,3-dimethyl-2-imidazolidinone is prepared via corresponding N-alkylmonoethanolamine and N-alkyldiethanolamine as intermediates, and the total molar amount of a molar feed amount of the monomethylamine included in the component (D), a molar feed amount of the monomethylamine part of the carbon dioxide compound of monomethylamine, said compound being component (E), and the double of a molar feed amount of the 1,3-dimethylurea, said 1,3-dimethylurea being component (F), is at least three folds of a molar feed amount of said ethylene oxide and the process further comprises:

(2) a first separation step of separating the reaction mixture obtained in the 1,3-dimethyl-2-imidazolidinone preparation step into a first fraction containing monomethylamine, carbon dioxide and a carbon dioxide compound of monomethylamine as main components, and also containing water; and a second fraction containing 1,3-dimethyl-2-imidazolidinone and high-boiling compounds with a higher boiling point than that of 1,3-dimethyl-2-imidazolidinone as main components, and also containing water;

(3) a second separation step of separating at least part of the second fraction in the first separation step into a first fraction containing water and low-boiling amines with a boiling point higher than that of water and lower than that of 1,3-dimethyl-2-imidazolidinone as main components; and a second fraction containing 1,3-dimethyl-2-imidazolidinone and said high-boiling compounds as main components;

(4) a third separation step of separating the second fraction in the second separation step into a first fraction containing 1,3-dimethyl-2-imidazolidinone as a main component; and a second fraction containing said high-boiling compounds as main components; and (5) a fourth separation step of separating the first fraction in the first separation step into a first fraction containing ammonia, dimethylamine, trimethylamine, a carbon dioxide compound of ammonia, a carbon dioxide compound of dimethylamine and a carbon dioxide compound of trimethylamine as main components, and also containing water; and a second fraction containing monomethylamine and a carbon dioxide compound of monomethylamine as main components, and also containing water, where at least part of the second fraction in the fourth separation step is supplied in the 1,3-dimethyl-2-imidazolidinone preparation step.

14. The process as claimed in claim 13, characterized in that the 1,3-dimethyl-2-imidazolidinone preparation step is carried out by:
(6) a first reaction step of heating ethylene oxide and at least one selected from the group consisting of the components (D), (E) and (F) at 50° C. or higher to prepare N-methyldiethanolamine and 2-(methylamino)ethanol; and
(7) a second reaction step of heating N-methyldiethanolamine and 2-(methylamino)ethanol prepared in the first reaction step with at least one selected from the group consisting of the components (D), (E) and (F) at 100° C. or higher to prepare 1,3-dimethyl-2-imidazolidinone, and the second fraction in the fourth separation step is supplied in said first reaction step and/or said second reaction step.

15. The process as claimed in claim 14, characterized in that in the fourth separation step, at least part of the first fraction in the first separation step is contacted with carbon dioxide, heated at 50° C. or higher, and separated by vapor-liquid separation to remove the first fraction in the fourth separation step into the gaseous phase and obtain the second fraction in the fourth separation step from the liquid phase.

16. The process as claimed in claim 13, characterized in that in the fourth separation step, at least part of the first fraction in the first separation step is contacted with carbon dioxide, heated at 50° C. or higher, and separated by vapor-liquid separation to remove the first fraction in the fourth separation step into the gaseous phase and obtain the second fraction in the fourth separation step from the liquid phase.

* * * * *